(12) United States Patent
Fox et al.

(10) Patent No.: US 8,808,294 B2
(45) Date of Patent: Aug. 19, 2014

(54) METHOD AND APPARATUS FOR A MULTIPLE TRANSITION TEMPERATURE IMPLANT

(75) Inventors: William Casey Fox, Pipe Creek, TX (US); David Joseph Pancratz, Helotes, TX (US)

(73) Assignee: William Casey Fox, Pipe Creek, TX (US)

( * ) Notice: Subject to any disclaimer, the term of this patent is extended or adjusted under 35 U.S.C. 154(b) by 970 days.

(21) Appl. No.: 12/283,074

(22) Filed: Sep. 9, 2008

(65) Prior Publication Data

US 2010/0063506 A1 Mar. 11, 2010

(51) Int. Cl.
*A61B 17/56* (2006.01)
*A61B 17/84* (2006.01)

(52) U.S. Cl.
USPC ............................................. 606/75; 606/78

(58) Field of Classification Search
USPC .................................................. 606/219, 220
See application file for complete search history.

(56) References Cited

U.S. PATENT DOCUMENTS

| | | | |
|---|---|---|---|
| 3,174,851 A | 3/1965 | Buehler et al. ................ | 75/170 |
| 4,047,524 A | 9/1977 | Hall ................................ | 128/69 |
| 4,170,990 A | 10/1979 | Baumgart et al. ........... | 128/92 B |
| 4,263,903 A | 4/1981 | Griggs .......................... | 128/92 B |
| 4,278,091 A | 7/1981 | Borzone ........................ | 128/334 |
| 4,321,002 A | 3/1982 | Froehlich ..................... | 411/457 |
| 4,434,796 A | 3/1984 | Karapetian et al. ........... | 128/335 |
| 4,454,875 A | 6/1984 | Pratt et al. .................... | 128/92 |
| 4,501,269 A | 2/1985 | Bagby ........................... | 606/61 |
| 4,570,623 A | 2/1986 | Ellison et al. ................. | 128/92 |
| 4,665,906 A | 5/1987 | Jervis ............................. | 128/92 |
| 4,723,540 A | 2/1988 | Gilmer, Jr. .................... | 128/92 |
| 4,756,711 A | 7/1988 | Mai et al. ...................... | 623/23 |
| 4,936,848 A | 6/1990 | Bagby .......................... | 623/17.16 |
| 5,002,563 A | 3/1991 | Pyka et al. ..................... | 606/222 |
| 5,015,247 A | 5/1991 | Michelson .................... | 606/61 |
| 5,015,255 A | 5/1991 | Kuslich ......................... | 128/898 |
| 5,046,513 A | 9/1991 | Gatturna et al. .............. | 128/898 |
| 5,053,038 A | 10/1991 | Sheehan ........................ | 606/75 |
| 5,059,193 A | 10/1991 | Kuslich ......................... | 606/61 |
| 5,067,957 A | 11/1991 | Jervis ............................ | 606/108 |
| 5,089,009 A | 2/1992 | Green ............................ | 606/219 |

(Continued)

OTHER PUBLICATIONS

Beynet, ,Patrick, "Production of a Fracture-Reducing Staple Using Ti—Ni Shape Memory Alloys," University of Poincare (Nancy1), France, 1994.

(Continued)

*Primary Examiner* — Nicholas Woodall
(74) *Attorney, Agent, or Firm* — Greenberg Traurig, LLP; Ross Spencer Garsson

(57) ABSTRACT

A shape-memory device manufactured from shape memory material includes multiple activation temperatures. The multiple activation temperatures arise from either the heat treatment of the device during manufacturing, or by combining different elements with different activation temperatures. To manufacture a shape-memory device with multiple activation temperatures, it is formed into a first shape. A first portion of the shape-memory device is heated to a first temperature, and a second portion of the shape-memory device is heated to a second temperature. The shape-memory device is then worked into a second shape. Accordingly, the first portion has a first transition temperature, and the second portion has a second transition temperature. In use, the shape-memory device is placed into a desired position. Energy is applied such that the first portion, second portion, or both portions are transformed.

2 Claims, 31 Drawing Sheets

(56) References Cited

U.S. PATENT DOCUMENTS

| | | | |
|---|---|---|---|
| 5,108,395 A | 4/1992 | Laurain | 606/61 |
| 5,209,756 A | 5/1993 | Seedhom et al. | 606/151 |
| 5,222,975 A | 6/1993 | Crainich | 606/219 |
| 5,246,443 A * | 9/1993 | Mai | 606/78 |
| 5,263,953 A | 11/1993 | Bagby | 606/61 |
| 5,304,204 A | 4/1994 | Bregen | 606/219 |
| 5,324,307 A | 6/1994 | Jarrett et al. | 606/219 |
| 5,342,396 A | 8/1994 | Cook | 606/219 |
| 5,352,229 A | 10/1994 | Goble et al. | 606/72 |
| 5,366,479 A | 11/1994 | McGarry et al. | 606/219 |
| 5,395,372 A | 3/1995 | Holt et al. | 606/61 |
| 5,449,359 A | 9/1995 | Groiso | 606/75 |
| 5,454,814 A | 10/1995 | Comte | 606/75 |
| 5,458,638 A | 10/1995 | Kuslich et al. | 623/17.11 |
| 5,484,437 A | 1/1996 | Michelson | 606/61 |
| 5,489,307 A | 2/1996 | Kuslich et al. | 128/898 |
| 5,489,308 A | 2/1996 | Kuslich et al. | 623/17.11 |
| 5,505,732 A | 4/1996 | Michelson | 606/61 |
| 5,522,899 A | 6/1996 | Michelson | 606/61 |
| 5,551,871 A | 9/1996 | Besselink et al. | 433/5 |
| 5,554,191 A | 9/1996 | Lahille et al. | 623/17.11 |
| 5,591,235 A | 1/1997 | Kuslich | 606/61 |
| 5,593,409 A | 1/1997 | Michelson | 606/61 |
| 5,597,378 A | 1/1997 | Jervis | 606/78 |
| D378,409 S | 3/1997 | Michelson | D24/145 |
| 5,609,635 A | 3/1997 | Michelson | 623/17.16 |
| 5,645,599 A | 7/1997 | Samani | 623/17 |
| 5,660,188 A | 8/1997 | Groiso | 128/898 |
| 5,665,122 A | 9/1997 | Kambin | 623/17.16 |
| 5,709,683 A | 1/1998 | Bagby | 606/61 |
| 5,720,748 A | 2/1998 | Kuslich et al. | 606/80 |
| 5,728,127 A | 3/1998 | Asher et al. | 606/61 |
| 5,776,199 A | 7/1998 | Michelson | 623/17.61 |
| 5,785,710 A | 7/1998 | Michelson | 606/61 |
| 5,785,713 A | 7/1998 | Jobe | 606/69 |
| 5,853,414 A | 12/1998 | Groiso | 606/75 |
| 5,860,973 A | 1/1999 | Michelson | 606/61 |
| 5,876,434 A | 3/1999 | Flomenblit | 623/1 |
| 5,885,287 A | 3/1999 | Bagby | 606/61 |
| 5,895,427 A | 4/1999 | Kuslich et al. | 128/898 |
| 5,941,880 A | 8/1999 | Errico et al. | 606/61 |
| 5,941,890 A | 8/1999 | Voegele et al. | 606/151 |
| 6,010,502 A | 1/2000 | Bagby | 606/61 |
| 6,056,749 A | 5/2000 | Kuslich | 606/61 |
| 6,083,242 A | 7/2000 | Cook | 606/219 |
| 6,086,589 A | 7/2000 | Kuslich et al. | 606/61 |
| 6,120,503 A | 9/2000 | Michelson | 606/61 |
| 6,123,705 A | 9/2000 | Michelson | 623/17.16 |
| 6,127,597 A | 10/2000 | Beyar et al. | 606/86 |
| 6,149,650 A | 11/2000 | Michelson | 623/17.16 |
| 6,149,686 A | 11/2000 | Kuslich et al. | 623/17.11 |
| 6,159,244 A | 12/2000 | Suddaby | 623/17.11 |
| 6,174,334 B1 | 1/2001 | Suddaby | 623/17.11 |
| 6,183,517 B1 | 2/2001 | Suddaby | 623/17.16 |
| 6,228,085 B1 | 5/2001 | Theken et al. | 606/61 |
| 6,241,770 B1 | 6/2001 | Michelson | 623/17.11 |
| 6,264,651 B1 | 7/2001 | Underwood et al. | 606/32 |
| 6,264,656 B1 | 7/2001 | Michelson | 606/61 |
| 6,277,112 B1 | 8/2001 | Underwood et al. | 606/32 |
| 6,283,961 B1 | 9/2001 | Underwood et al. | 606/41 |
| 6,287,343 B1 | 9/2001 | Kuslich et al. | 623/17.11 |
| 6,302,914 B1 | 10/2001 | Michelson | 623/17.16 |
| RE37,479 E | 12/2001 | Kuslich | 623/17.11 |
| 6,325,805 B1 | 12/2001 | Ogilvie et al. | 606/75 |
| 6,332,895 B1 | 12/2001 | Suddaby | 623/17.11 |
| 6,364,880 B1 | 4/2002 | Michelson | 606/61 |
| 6,371,986 B1 | 4/2002 | Bagby | 623/17.11 |
| 6,391,058 B1 | 5/2002 | Kuslich et al. | 623/17.11 |
| 6,395,035 B2 | 5/2002 | Bresina et al. | 623/17.15 |
| 6,432,107 B1 | 8/2002 | Ferree | 606/61 |
| 6,436,098 B1 | 8/2002 | Michelson | 606/61 |
| 6,436,102 B1 | 8/2002 | Ralph et al. | 606/90 |
| 6,440,135 B2 | 8/2002 | Orbay et al. | 606/69 |
| 6,447,544 B1 | 9/2002 | Michelson | 623/17.16 |
| 6,447,545 B1 | 9/2002 | Bagby | 623/12.16 |
| 6,447,547 B1 | 9/2002 | Michelson | 623/17.16 |
| 6,447,548 B1 | 9/2002 | Ralph et al. | 623/17.16 |
| 6,451,019 B1 | 9/2002 | Zucherman et al. | 606/61 |
| 6,454,807 B1 | 9/2002 | Jackson | 623/17.15 |
| 6,468,274 B1 | 10/2002 | Alleyne et al. | 606/41 |
| 6,471,725 B1 | 10/2002 | Ralph et al. | 623/17.16 |
| 6,478,801 B1 | 11/2002 | Ralph et al. | 606/99 |
| 6,478,823 B1 | 11/2002 | Michelson | 623/17.16 |
| 6,485,517 B1 | 11/2002 | Michelson | 623/17.11 |
| 6,488,710 B2 | 12/2002 | Besselink | 623/17.15 |
| 6,491,724 B1 | 12/2002 | Ferree | 632/17.11 |
| 6,500,173 B2 | 12/2002 | Underwood et al. | 606/32 |
| 6,500,205 B1 | 12/2002 | Michelson | 623/17.16 |
| 6,517,544 B1 | 2/2003 | Michelson | 606/80 |
| 6,537,279 B1 | 3/2003 | Michelson | 606/79 |
| 6,537,320 B1 | 3/2003 | Michelson | 623/17.11 |
| 6,540,741 B1 | 4/2003 | Underwood et al. | 606/32 |
| 6,554,864 B2 | 4/2003 | Ralph et al. | 623/17.11 |
| 6,558,386 B1 | 5/2003 | Cragg | 606/61 |
| 6,558,390 B2 | 5/2003 | Cragg | 606/80 |
| 6,558,423 B1 | 5/2003 | Michelson | 623/17.11 |
| 6,562,047 B2 | 5/2003 | Ralph et al. | 606/99 |
| 6,572,619 B2 | 6/2003 | Santilli | 606/61 |
| 6,607,530 B1 | 8/2003 | Carl et al. | 606/61 |
| 6,607,559 B2 | 8/2003 | Ralph et al. | 623/17.16 |
| 6,616,666 B1 | 9/2003 | Michelson | 606/61 |
| 6,620,155 B2 | 9/2003 | Underwood et al. | 606/32 |
| 6,623,525 B2 | 9/2003 | Ralph et al. | 623/17.16 |
| 6,648,915 B2 | 11/2003 | Sazy | 623/17.11 |
| 6,652,584 B2 | 11/2003 | Michelson | 623/17.11 |
| 6,656,178 B1 | 12/2003 | Veldhuizen et al. | 606/616 |
| 6,689,167 B2 | 2/2004 | Bagby | 623/17.11 |
| 6,695,760 B1 | 2/2004 | Winkler et al. | 600/7 |
| 6,706,044 B2 | 3/2004 | Kuslich et al. | 606/61 |
| 6,709,458 B2 | 3/2004 | Michelson | 623/17.15 |
| 6,712,811 B2 | 3/2004 | Underwood et al. | 606/31 |
| 6,716,247 B2 | 4/2004 | Michelson | 623/17.16 |
| 6,723,131 B2 | 4/2004 | Muschler | 623/23.51 |
| 6,726,684 B1 | 4/2004 | Woloszko et al. | 606/32 |
| 6,730,127 B2 | 5/2004 | Michelson | 623/17.16 |
| 6,733,535 B2 | 5/2004 | Michelson | 623/17.16 |
| 6,736,799 B1 | 5/2004 | Erbe et al. | 604/181 |
| 6,740,119 B2 | 5/2004 | Ralph et al. | 623/17.16 |
| 6,743,255 B2 | 6/2004 | Ferree | 623/17.11 |
| 6,749,636 B2 | 6/2004 | Michelson | 623/17.16 |
| 6,758,849 B1 | 7/2004 | Michelson | 606/61 |
| 6,767,367 B1 | 7/2004 | Michelson | 623/17.16 |
| 6,773,437 B2 | 8/2004 | Ogilvie et al. | 606/75 |
| 6,786,930 B2 | 9/2004 | Biscup | 623/16.11 |
| 6,793,679 B2 | 9/2004 | Michelson | 623/17.16 |
| 6,800,092 B1 | 10/2004 | Williams et al. | 623/17.11 |
| 6,805,716 B2 | 10/2004 | Ralph et al. | 623/17.16 |
| 6,808,537 B2 | 10/2004 | Michelson | 623/17.15 |
| 6,814,756 B1 | 11/2004 | Michelson | 623/17.11 |
| 6,821,298 B1 | 11/2004 | Jackson | 623/17.15 |
| 6,827,740 B1 | 12/2004 | Michelson | 623/17.11 |
| 6,827,743 B2 | 12/2004 | Eisermann et al. | 623/23.54 |
| 6,835,206 B2 | 12/2004 | Jackson | 623/17.11 |
| 6,849,093 B2 | 2/2005 | Michelson | 623/17.15 |
| 6,863,689 B2 | 3/2005 | Ralph et al. | 623/17.16 |
| 6,890,355 B2 | 5/2005 | Michelson | 623/17.11 |
| 6,890,356 B2 | 5/2005 | Ralph et al. | 623/17.16 |
| 6,896,680 B2 | 5/2005 | Michelson | 606/90 |
| 6,921,403 B2 | 7/2005 | Cragg et al. | 606/86 |
| 6,923,810 B1 | 8/2005 | Michelson | 606/61 |
| 6,923,811 B1 | 8/2005 | Carl et al. | 606/61 |
| 6,923,830 B2 | 8/2005 | Michelson | 623/17.16 |
| 6,929,640 B1 | 8/2005 | Underwood et al. | 606/32 |
| 6,962,606 B2 | 11/2005 | Michelson | 623/17.16 |
| 6,966,912 B2 | 11/2005 | Michelson | 606/80 |
| 6,969,390 B2 | 11/2005 | Michelson | 606/61 |
| 6,972,019 B2 | 12/2005 | Michelson | 606/61 |
| 6,972,035 B2 | 12/2005 | Michelson | 623/17.11 |
| 6,976,949 B2 | 12/2005 | Winkler et al. | 600/7 |
| 6,981,975 B2 | 1/2006 | Michelson | 606/99 |
| 6,986,772 B2 | 1/2006 | Michelson | 606/90 |
| 7,008,453 B1 | 3/2006 | Michelson | 623/17.16 |
| 7,014,633 B2 | 3/2006 | Cragg | 604/500 |
| 7,018,415 B1 | 3/2006 | McKay | 623/17.15 |

(56) References Cited

U.S. PATENT DOCUMENTS

| | | | |
|---|---|---|---|
| 7,033,394 B2 | 4/2006 | Michelson | 623/17.11 |
| 7,041,135 B2 | 5/2006 | Michelson | 623/17.11 |
| 7,044,971 B2 | 5/2006 | Suddaby | 623/17.15 |
| 7,056,342 B2 | 6/2006 | Michelson | 623/17.11 |
| 7,060,073 B2 | 6/2006 | Frey et al. | 606/85 |
| 7,066,961 B2 | 6/2006 | Michelson | 623/17.16 |
| 7,097,648 B1 | 8/2006 | Gluberman et al. | 606/99 |
| 7,104,986 B2 | 9/2006 | Houda et al. | 606/32 |
| 2003/0191528 A1* | 10/2003 | Quijano et al. | 623/2.37 |

OTHER PUBLICATIONS

Beynet, Patrick, "Bibliography of Shape Memory Alloys," 1993-1994, Laboratory of Science and Engineering of Surfaces, University of Poincare (Nancy1), France.

Knox, Glenn W. and Reitan, Harlan, "Shape-Memory Stapes Prosthesis for Otosclerosis," Laryngscope 115, Aug. 2005.

Ryhanen, J., et al., "Bone healing and Mineralization, Implant Corrosion, and Trace Metals after Nickel-Titanium Shape Memory Metal Intramedullary Fixation," John Wiley and Sons, Inc., J Biomed Res, 47, 472-482, 1999.

* cited by examiner

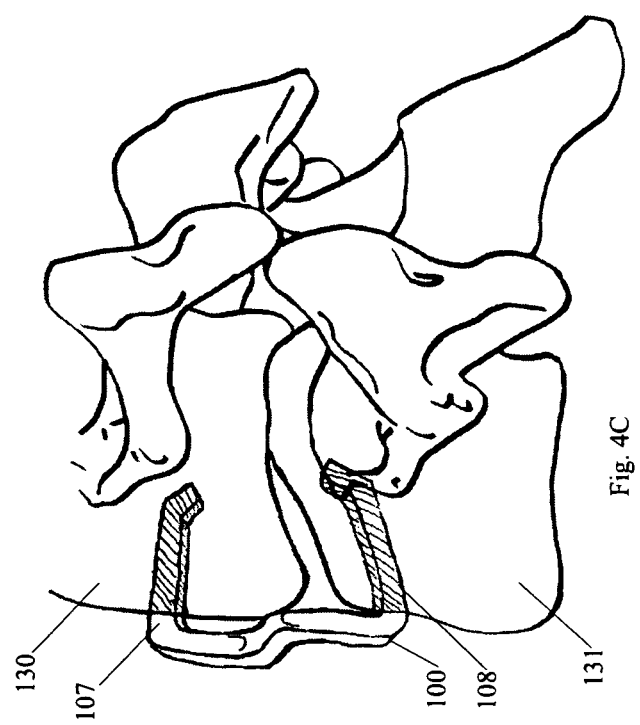

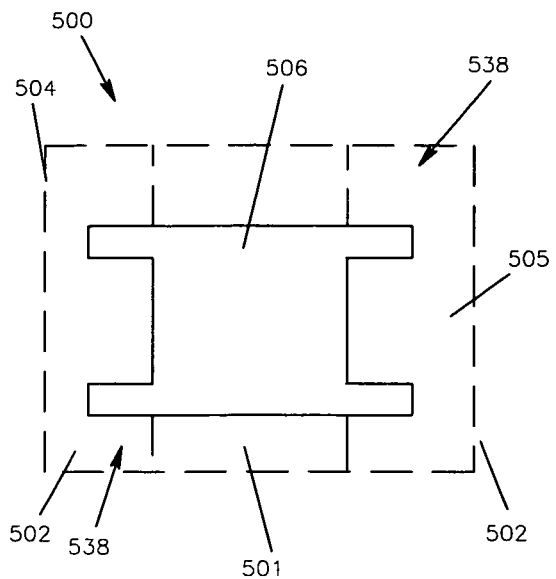
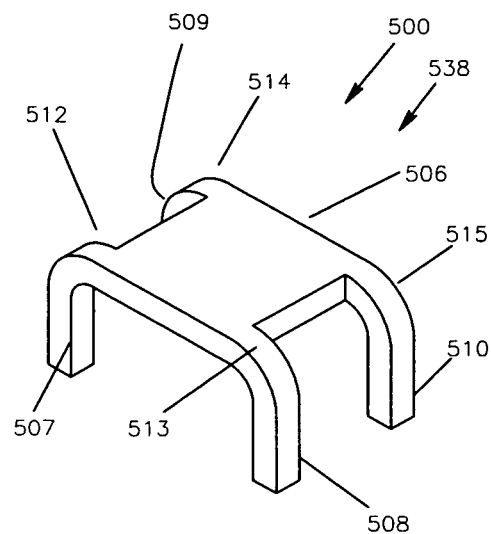
Fig. 17A  Fig. 17B
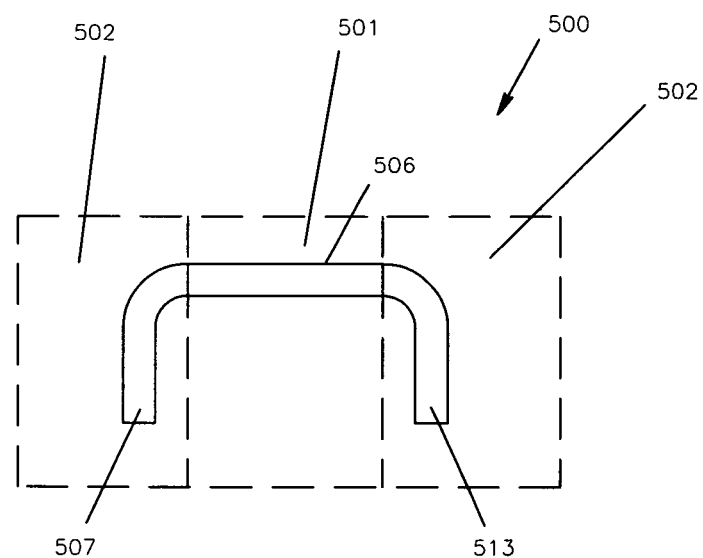
Fig. 17C

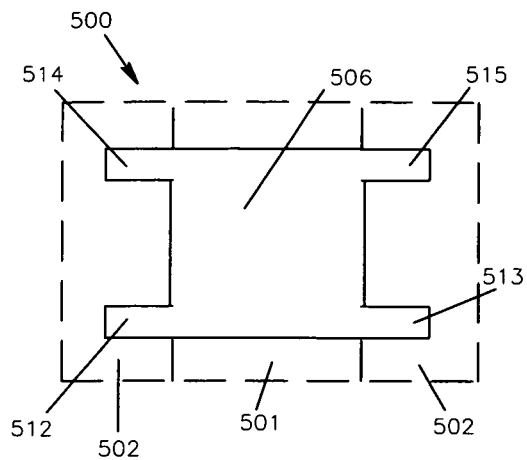
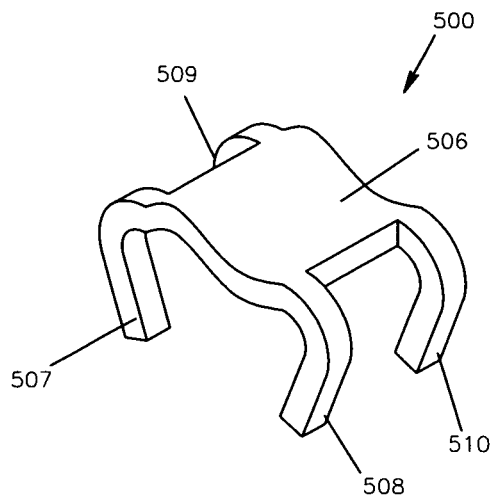
Fig. 19A    Fig. 19B
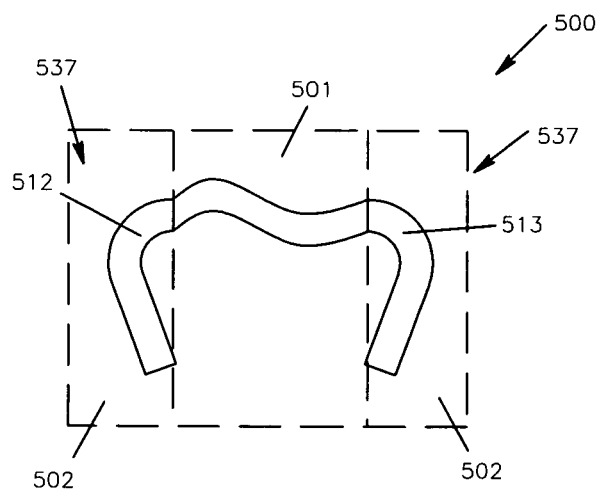
Fig. 19C

62 — Shape set the implant so that one portion has a shape memory, while another portion has no shape memory. The portion of the implant that has no shape memory can be left either permanently in the martensite or austenite state.

64 — Create a permanent bend in the portion of the implant that has no shape memory so that it conforms to the anatomy.

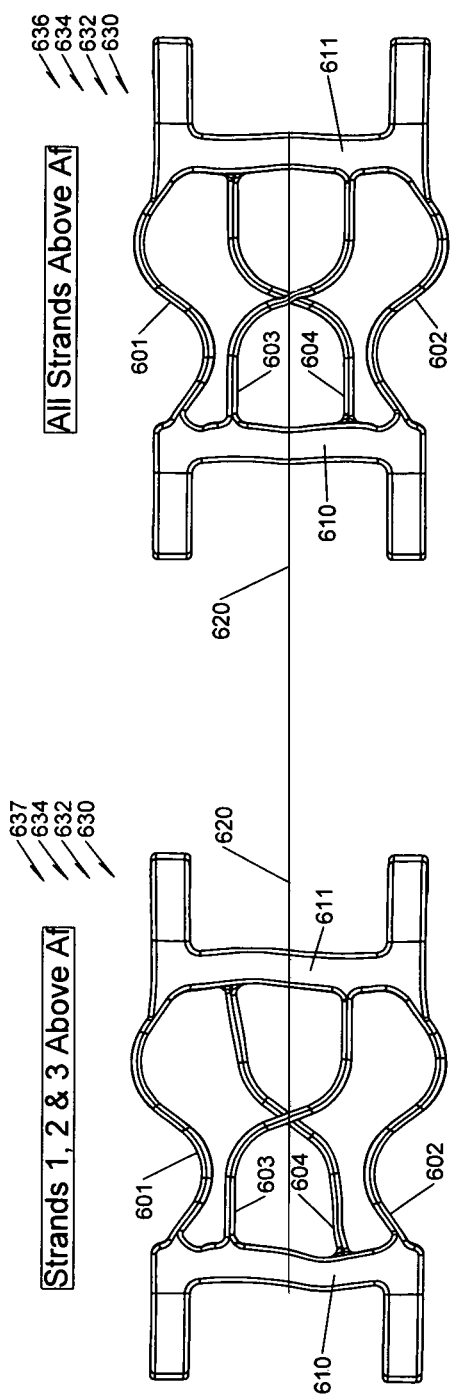

METHOD AND APPARATUS FOR A MULTIPLE TRANSITION TEMPERATURE IMPLANT

BACKGROUND OF THE INVENTION

1. Field of the Invention

The present invention relates to implants for the human body and, more particularly, but not by way of limitation, to methods and an apparatus for an implant having multiple transition temperatures.

2. Description of the Related Art

Shape memory alloys such as nitinol have been well known since their development in 1965 by Buehler and Wiley (U.S. Pat. No. 3,174,851). Other metals, such as AuCd, FePt.sub.3, beta Brass, and InTI, exhibit shape memory behavior. These materials have the property of changing shape in response to a change in material temperature. This shape change potential is imparted into the memory metal device through a series of heat treatments.

The transition temperature range is imparted to the material through varying mixtures of intermetallic compounds such as nickel-titanium and heat treatment. The heat treatment methods for the material generally consist of a high temperature setting of the desired final shape of a device followed by a low temperature straining of the device to a second shape. Then, when the device is in the second shape and brought to the transition temperature, the device returns to the preprogrammed final shape. The shape change occurs due to the transition of the material from a martensitic to austenitic phase microstructure. These heat-initiated changes cause gross changes in the shape of the implant formed from the memory metal.

Shape memory alloys have been used for a wide range of industrial and medical applications. Medical applications include but are not limited to: catheter, intrauterine contraceptive device, gastrointestinal compression clip, blood vessel filter, coronary artery stent, skin staple, bone staple, and bone plate. In medical applications, shape memory alloys are generally designed so that they change shape once when heated to and beyond a specific temperature. The implants and devices are designed as a whole to transition once from martensite to partial or full austenite. For example, Fox (U.S. Pat. No. 7,240,677) describes a method for force, displacement, and rate control of shaped memory metal implants. Nevertheless, the implants and techniques in this patent do not describe multiple transition temperatures in the same device.

However, in many instances, it may be desirable for an implant or device to have either multiple transition temperatures, or multiple elements that transition at different temperatures. The existence of multiple transition temperatures would allow, for example, complex devices that can be heated first to one shape, and then heated further to additional shapes. Medical devices in orthopedics could be designed so that they undergo sequential shape changes for complex treatment of bones. Devices could also be designed such that part of the device is intentionally left in martensite. A device that has a portion that is always martensitic would be helpful in creating implants that can be deformed to conform to the curvature of bone. Other devices could be designed such that there is a shape changing portion that is martensitic at room temperature, and a second portion that does not change shape when heat is applied because it is always austenitic at normal temperatures.

Accordingly, a shape memory implant or device that features multiple transition temperatures or multiple elements with different transition temperatures would be beneficial to surgeons, as well as persons requiring bone surgeries, because the shape changing features of the device can be more complex and sequentially applied.

SUMMARY OF THE INVENTION

The present invention is a device made from a shape memory material that has the characteristic of having multiple transition temperatures. The presence of multiple transition temperatures allows shape changing devices to be designed that feature more complex shape changes, or shape changes that are applied in sequence. The present invention consists of methods for heat treating shape memory materials, and methods for attaching materials of different transition temperature characteristics.

The presence of multiple transition temperatures may be accomplished in several ways. A shape memory alloy device of may be heat treated such that it has multiple transition temperatures, or elements of a shape memory alloy device may include different temperature transition characteristics. These different elements can be shape memory materials that are of different elemental composition, or elements that are heat treated differently.

In accordance with the present invention, a shape memory device is formed into a first shape. A first portion of the shape-memory device is heated to a first temperature, and a second portion of the shape memory device is heated to a second temperature. The shape-memory device is then worked into a second shape. Accordingly, the first portion has a first transition temperature, and the second portion has a second transition temperature. In the preferred embodiment, the second transition temperature is higher than the first transition temperature. The shape memory device may be formed as a single component, or, alternatively, the first portion and the second portion may be formed as separate components, whereby the separate components are coupled together to create the shape-memory device having multiple transition temperatures.

In use, the shape memory device is placed into a desired position. A first activation energy is applied to the first portion such that the first portion transitions from the second shape to an end use shape. Similarly, a second activation energy is applied to the second portion such that the second portion transitions from the second shape to an end use shape. The end use shape is any shape along the transition from the second shape up to and including a first shape.

It is therefore an object of the present invention to provide a shape memory device including multiple transition temperatures.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF THE DRAWINGS

FIG. 4C provides a frontal view of the shape-memory device after a first portion has been activated according to the first embodiment.

FIG. 17A provides a top view of a shape-memory device including a single transition temperature and a permanently formed section according to a fifth embodiment.

FIG. 17B provides a perspective view of the shape-memory device including the single transition temperature and the permanently formed section according to the fifth embodiment.

FIG. 17C provides a frontal view of the shape-memory device including the single transition temperature and the permanently formed section according to the fifth embodiment.

FIG. 19A provides a top view of a shape-memory device including the single transition temperature and the permanently formed section after forming the formed section and activating a second portion according to the fifth embodiment.

FIG. 19B provides a perspective view of the shape-memory device including the single transition temperature and the permanently formed section after forming the formed section and activating the second portion according to the fifth embodiment.

FIG. 19C provides a frontal view of the shape-memory device including the single transition temperature and the permanently formed section after forming the formed section and activating the second portion according to the fifth embodiment.

FIG. 21E provides a top view of the shape-memory device having a first, second, and third portions activated according to the second alternative embodiment.

FIG. 21F provides a top view of the shape-memory device having all portions activated according to the second alternative embodiment.

DETAILED DESCRIPTION OF THE PREFERRED EMBODIMENTS

Figure 1A:
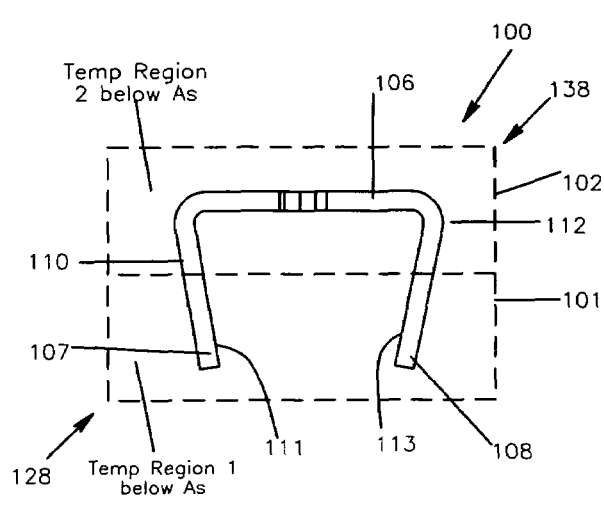
FIG. 1A provides a frontal view of a shape-memory device including multiple transition temperatures according to a first embodiment.
Figure 1B:
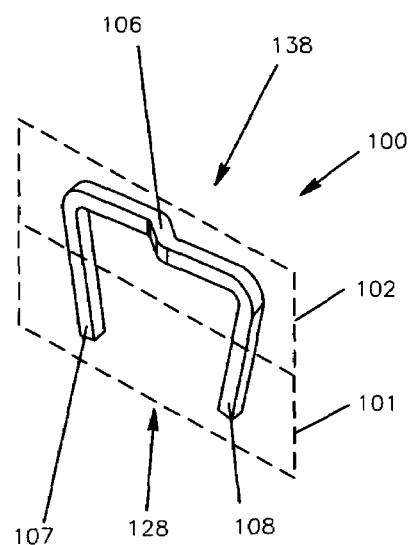
FIG. 1B provides a perspective view of the shape-memory device including multiple transition temperatures according to the first embodiment.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Shape-memory devices may be constructed from virtually any material exhibiting a shape-memory effect. Examples of shape-memory effect materials include, but are not limited to nitinol, AuCd, $FePt_3$, beta Brass, and InTI. Shape-memory effect materials allow an object to be: formed in an original shape; deformed while in a martensitic state; heated to a point where the deformed object phase changes from the martensitic state to an austenitic state, thereby returning the deformed object to its original shape; and cooled such that the object retains the original shape. Accordingly, the shape-memory devices are formed in an original or first shape, and heat treated to set the original shape. The shape-memory devices, while cold and in the martensitic phase, are then deformed to a second shape. Next, the shape-memory devices are heated to a prescribed transition temperature until they phase change to an austenitic phase, thereby returning from the deformed or second shape to the original or first shape. Finally, the shape-memory devices cool whereby the shape-memory devices retain the original first shape.

In this invention, shape-memory devices with a single transition temperature are expanded to include shape-memory devices with multiple transition temperatures. The move to multiple transition temperatures requires the recognition that a shape-memory device of a homogeneous material may be manipulated through varied heat treatment processes, thereby creating portions on the homogeneous material that react differently upon the application of activation energy. Alternatively, a shape memory device may be constructed from multiple components, wherein each component includes a respective transition temperature, thereby providing the shape memory device with multiple transition temperatures.

As shown in FIGS. 1A through 3B, a shape-memory device 100 includes a first portion 101 having a first transition temperature and a second portion 102 having a second transition temperature. In this example, the shape-memory device 100 is a staple that may be utilized as an implant, and includes a bridge 106, a first leg 107, and a second leg 108. The first and second legs 107-108 are disposed on opposite ends of the bridge 106. The first leg 107 includes an upper segment 110 and a lower segment 111, and the second leg 108 includes an upper segment 112 and a lower segment 113. The lower segments 111 and 113 include an end that contracts inward when activation energy is applied. Also in this embodiment, the bridge 106 contracts upon the application of activation energy, thereby drawing the legs 107-108 closer.

The first portion 101 includes the lower segments 111 and 113 of the legs 107-108, including the ends that contract inward upon the application of energy. The first portion 101 further includes a first shape 127 and a second shape 128, whereby the ends of the first and second legs move inward when the temperature of the first portion 101 elevates toward the first activation temperature.

The second portion 102 includes the bridge 106 and the upper segments 110 and 112 of the legs 107-108. The second portion 102 also includes a first shape 137 and a second shape 138, whereby the bridge 106 commences to contract when the temperature of the second portion 102 nears the second activation temperature, and is in the first shape 137 when the second portion 102 reaches the second transition temperature. While this embodiment has been shown with the first portion 101 and the second portion 102 interfacing at a central portion of the legs 107-108, one of ordinary skill in the art will recognize that virtually any point may be utilized as a boundary between the first portion 101 and the second portion 102, dependent upon fixture designs, component designs, heat treatment jig designs, and the like.

While this embodiment has been shown with the shape-memory device 100 having two portions 101 and 102 moving from the second shapes 128 and 138 to the first shape 127 and 137, respectively, it should be apparent that both portions 101 and 102 are usable at virtually any point along the transition between the second shapes 128 and 138 and the first shapes 127 and 137, respectively. Accordingly, an end-use shape may designate any shape between the second shapes 128 and 138, up to and including the first shapes 127 and 137, respectively. The amount of heat energy applied to the deformed shape determines the amount of transition from the second shapes 128 and 138 to the first shapes 127 and 137, respectively.

While the shape memory device 100 has been shown with a first portion 101 activating before the second portion 102, one of ordinary skill in the art will recognize that the second portion 102 may be activated before the first portion 101, if so desired. Accordingly, the bridge 106 may contract before the legs 107-108. Further, a shape memory device including more than two portions may activate the portions in substantially any order to achieve varied results.

Figure 2A:
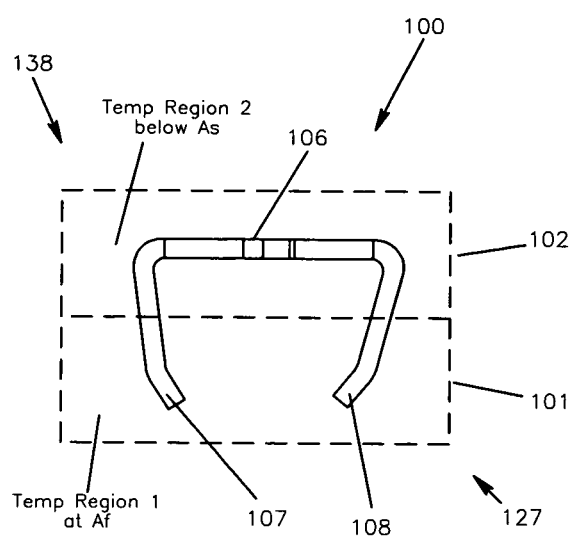
FIG. 2A provides a frontal view of the shape-memory device after a first transition temperature has been activated according to the first embodiment.
Figure 2B:
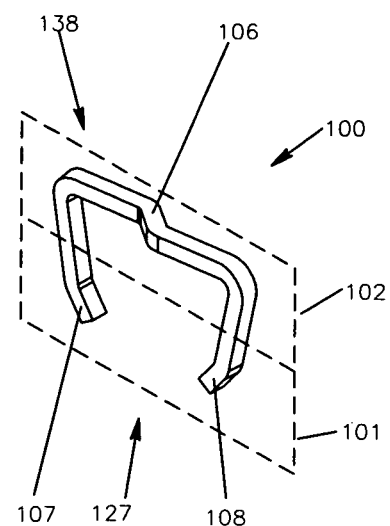
FIG. 2B provides a perspective view of the shape-memory device after the first transition temperature has been activated according to the first embodiment.

As shown in FIG. 1A, both the first portion 101 and the second portion 102 of the shape-memory device 100 are disposed in the second shapes 128 and 138, at temperatures below the commencement point for Austenite to form ($A_s$). FIG. 2A provides an illustration of the shape-memory device 100 after heat energy at the first transition temperature has been applied to the first portion 101. In this configuration, the heat energy has been delivered to the first portion 101, thereby raising the temperature of the first portion 101 of the shape-memory device 100 to the point where the entire first portion 101 is Austenite ($A_F$-First Portion). At temperature $A_F$-First Portion, the first portion 101 has fully transitioned to the first shape 127, wherein the ends of the legs 107 and 108 contract inward. As shown in FIG. 2A, the second portion 102 remains in the second shape 138, because the transition temperature for the second portion 102 is higher than the transition temperature for the first portion 101.

Figure 3A:
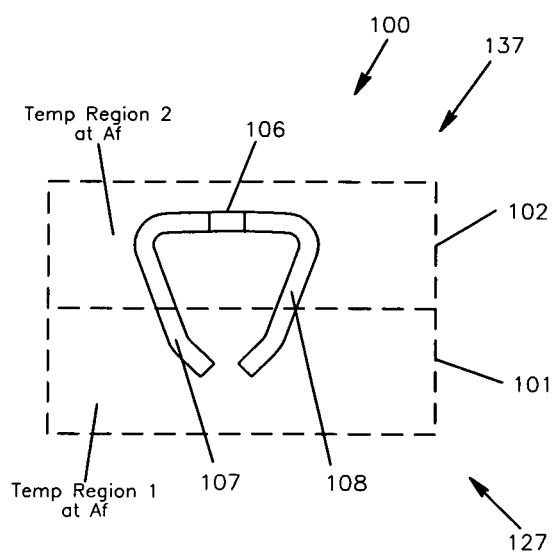
FIG. 3A provides a frontal view of the shape-memory device after the first transition temperature and a second transition temperature have been activated according to the first embodiment.
Figure 3B:
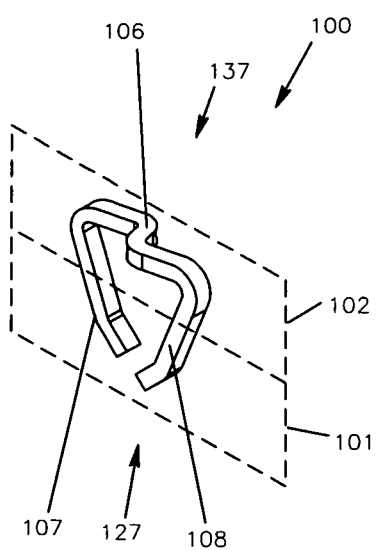
FIG. 3B provides a perspective view of the shape-memory device after the first transition temperature and the second transition temperature have been activated according to the first embodiment.

Upon the continued application of heat energy to the shape-memory device 100 above the $A_s$-Second Portion temperature, the second portion 102 commences to shape change, and continues to shape change until the $A_F$-Second Portion temperature is reached, at which point the bridge 106 has fully contracted to the first shape 137, as shown in FIGS. 3A-3B.

Figure 4A:
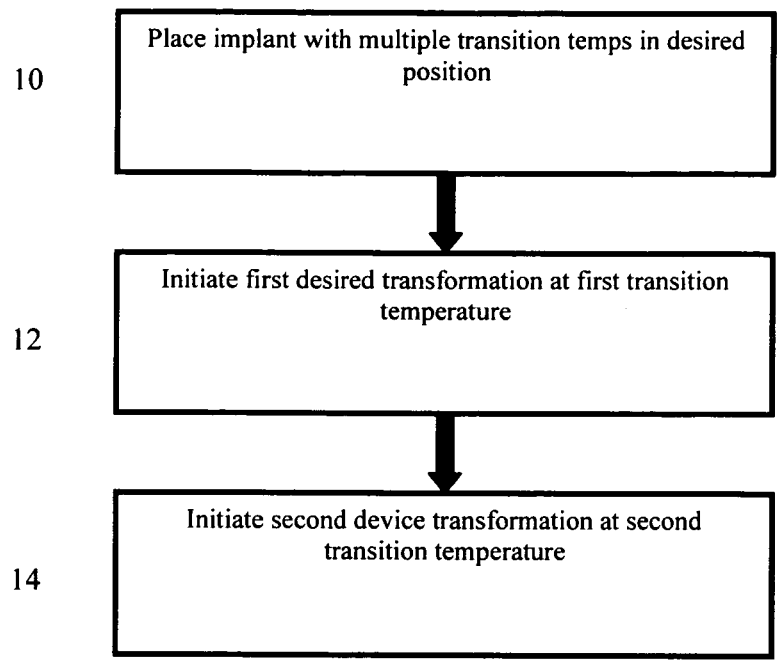
FIG. 4A provides a flowchart illustrating the method steps for utilizing the shape-memory device including multiple transition temperatures according to the first embodiment.

FIG. 4A provides a flowchart illustrating the method steps for utilizing the shape-memory device 100 having multiple activation temperatures. The process commences with the placement of the shape-memory device 100 into a desired position, step 10. The operator must then deliver a first activation energy to raise the temperature of a first portion 101 to at least temperature $A_F$-First Portion, thereby forcing the first portion 101 of the shape-memory device 100 to move from the second shape 128 to the first shape 127, step 12. The operator then delivers a second activation energy to the second portion 102 of the shape-memory device 100 to reach $A_F$-Second Portion, at which point the second portion 102 has shape changed from the second shape 138 to the first shape 137, step 14. At that point, both transition temperatures have been reached.

In cases where the shape-memory device 100 is implanted into a live body, the first and second transition temperatures may be below nominal body temperatures, above nominal body temperatures, or a combination of both. One of ordinary skill in the art will recognize that virtually all combinations may be utilized in a living body for varied results, including partial alignment of bones, fine alignment of bones, securing to bones, aids in bone fusion, and the like. Illustratively, an implant as shown in FIGS. 1A through 3B may have characteristics wherein the first portion 101 transition temperature is below the nominal body temperature, and the transition temperature of the second portion 102 is above the nominal body temperature. In this case, the first portion 101 would commence to shape change upon the insertion of the implant into the living body, and the second portion 102 would be activated to draw attached objects together. Upon heating of the implant to nominal body temperature, the first portion 101 shape changes to the first shape 127, thereby further securing the implant to attached structure, including bones or other restraint components.

One of ordinary skill in the art will recognize that each of the portions 101 or 102 of the shape-memory device 100 may be activated independently, together, or only one transition may be deemed necessary, dependent upon site-specific conditions, or desires of the operator.

Figure 4B:
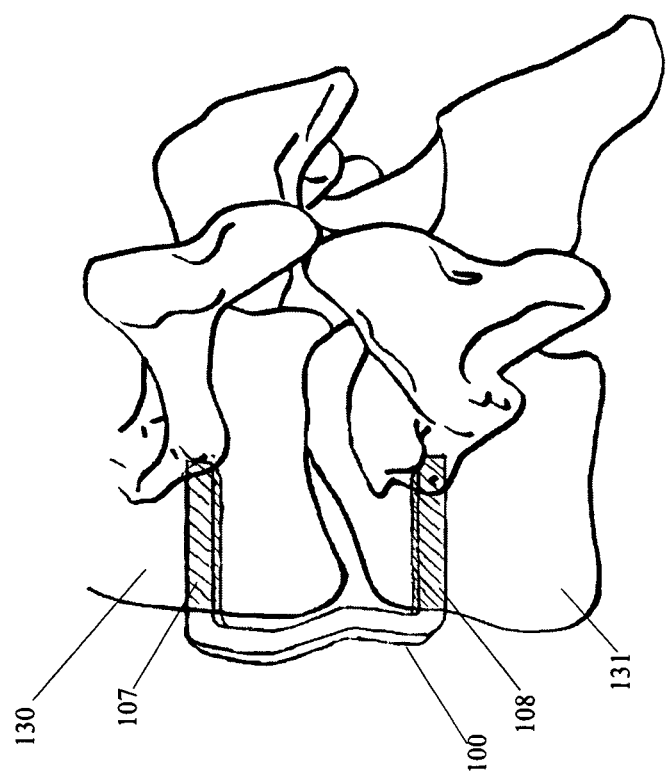
FIG. 4B provides a frontal view of the shape-memory device before activation, and installed into a first and second bone according to the first embodiment.
Figure 4D:
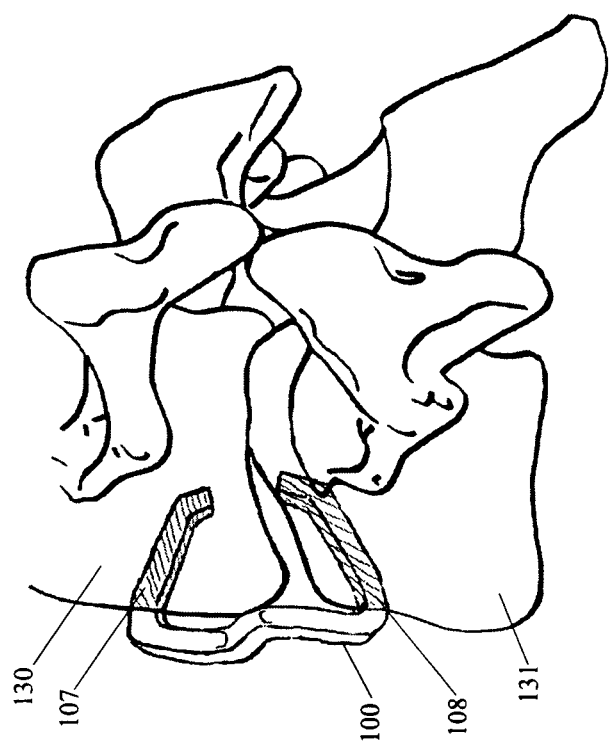
FIG. 4D provides a frontal view of the shape-memory device after a second portion has been activated according to the first embodiment.

The method steps for utilizing a shape-memory device 100 under in vivo conditions follows the method flowchart shown in FIG. 4A. As shown in step 10, a surgeon places the shape-memory device 100 having multiple transition temperatures into the body. As shown in FIG. 4B, the legs 107-108 of the shape-memory device 100 are installed into a first bone 130 and a second bone 131. The surgeon then utilizes any suitable necessary transition device to initiate a first desired transformation of a first portion 101 of the implant, as shown in FIG. 4C. One of ordinary skill in the art will recognize that multiple forms of heat energy are commonly available, including body heat, heating probes, and may be utilized at varying points to achieve desired results. Illustratively, the surgeon may utilize body heat to deliver energy to the first portion, and may utilize heating probes as the activation energy for a second portion 102. In this specific example, the ends of the legs 107-108 are activated first, thereby securing the shape-memory device 100 to the bones 130-131. Step 14 provides for utilizing a necessary transition device to initiate the second desired transformation, thereby shape-changing the second portion 102 of the implant toward the respective first shape 137, as shown in FIG. 4D.

In the manufacturing process, the shape-memory device 100 is formed in a desired first shape and heat treated in a heat treatment jig 120 having a first platen 121 and a second platen 122. The first platen 121 is disposed adjacent to the first portion 101 of the shape-memory device 100, and the second platen 122 is disposed adjacent to the second portion 102 of the shape-memory device 100. In this specific example, the first platen 121 is constructed from a different material than the second platen 122, and therefore has different thermal conductivity properties. Accordingly, the first portion 101 and the second portion 102 receive different heat treatments from the first platen 121 and the second platen 122.

Alternatively, the first platen 121 and the second platen 122 may be formed from like materials, wherein at least one is altered to limit thermal conduction to a mating shape-memory device 100. Illustratively, a first platen 121 may include a fluid passage 123 for flowing a fluid to cool the first platen 121. In such a case, the cooled platen would be at a different temperature than the unaltered platen, thereby forcing the first and second platens 121-122 to deliver varied heat treatments to the shape-memory device 100 disposed within the heat treatment jig 120. One of ordinary skill in the art will recognize that the heat treatment of a component may also be affected by the duration of the heat treatment.

Figure 5A:
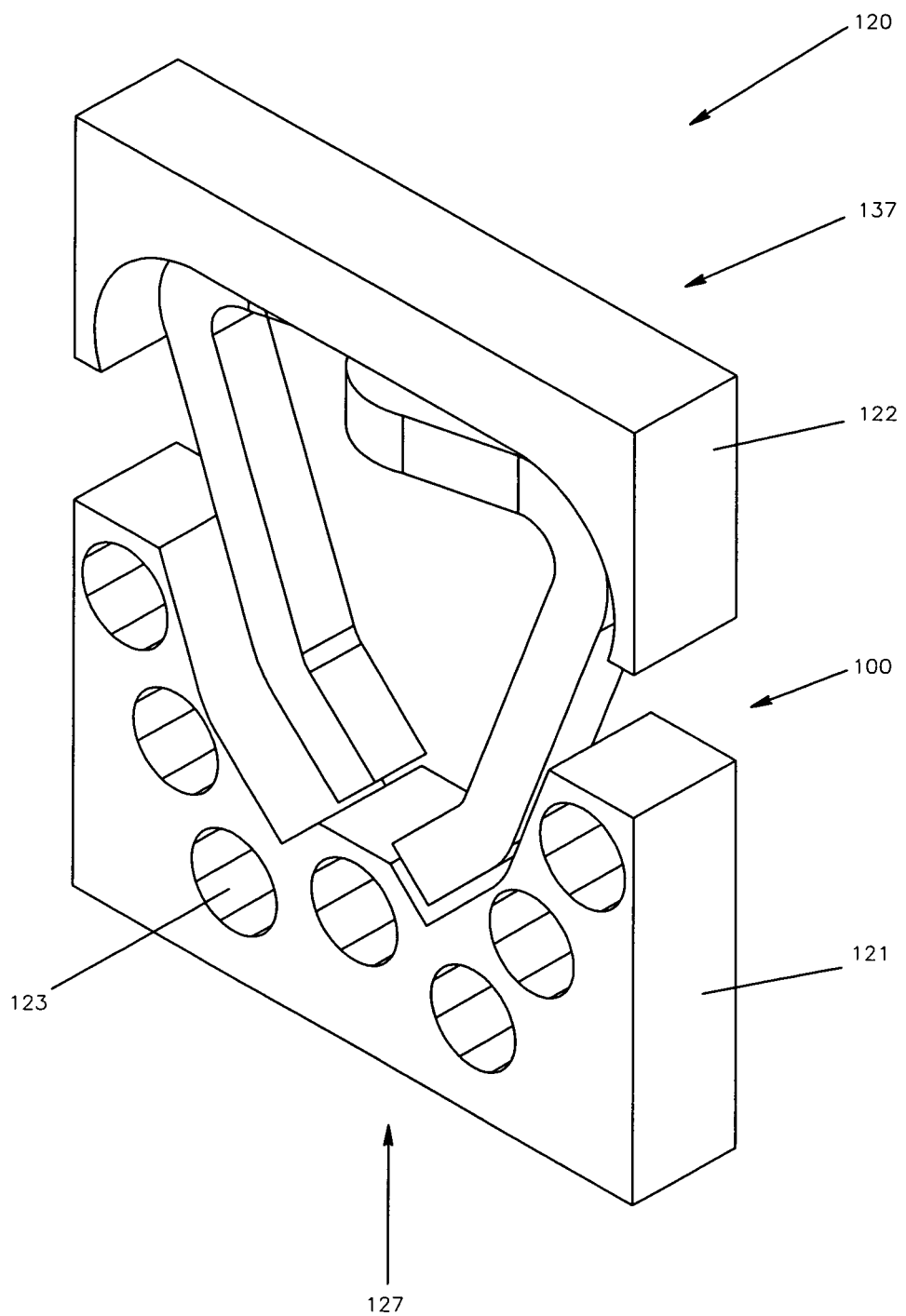
FIG. 5A provides a perspective view of a heat treatment jig according to the first embodiment.
Figure 5B:
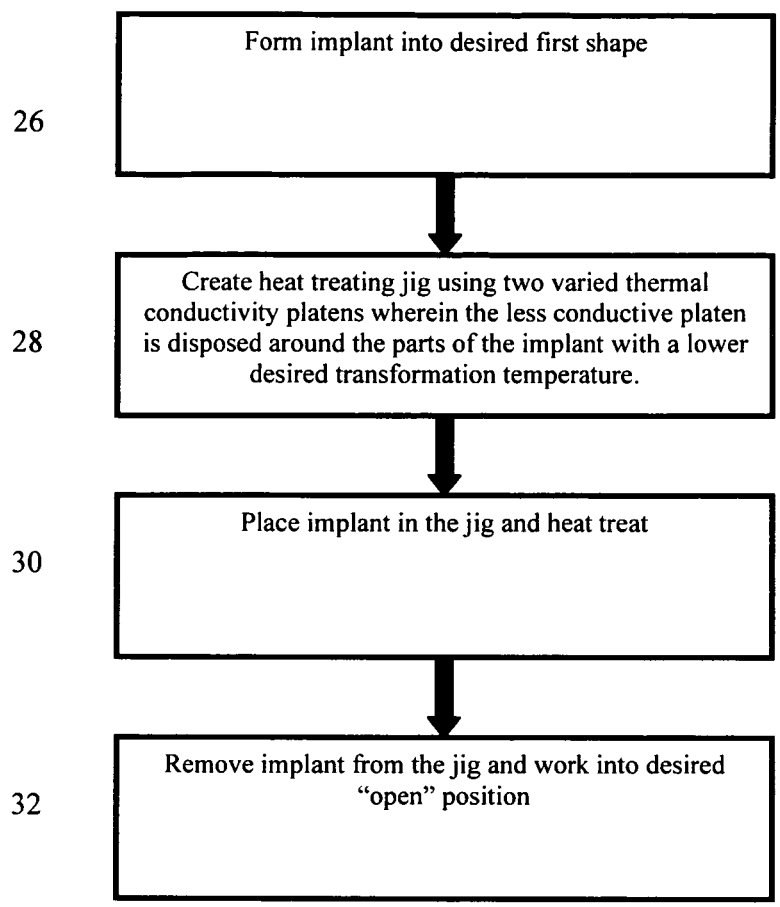
FIG. 5B provides a flowchart illustrating the method steps for manufacturing the shape-memory device according to the first embodiment.

FIG. 5B provides a method flowchart illustrating the method steps for creating a shape-memory device 100 having multiple transition temperatures. The process commences with creating a shape-memory device 100 that is formed into a desired first shape 127 and 137, step 26. Step 28 provides for creating a heat treating jig 120 including platens 121-122 having varied thermal conduction properties, either naturally or artificially induced, wherein the less conductive material is disposed around the portions of the shape-memory device 100 with a lower desired transformation temperature. Step 30 provides for placing the shape-memory device 100 into the jig 120 and heat treating the shape-memory device 100. In step 32, the shape-memory device 100 is removed from the jig 120 and worked into the desired second shapes 128 and 138, respectively.

Figure 5C:
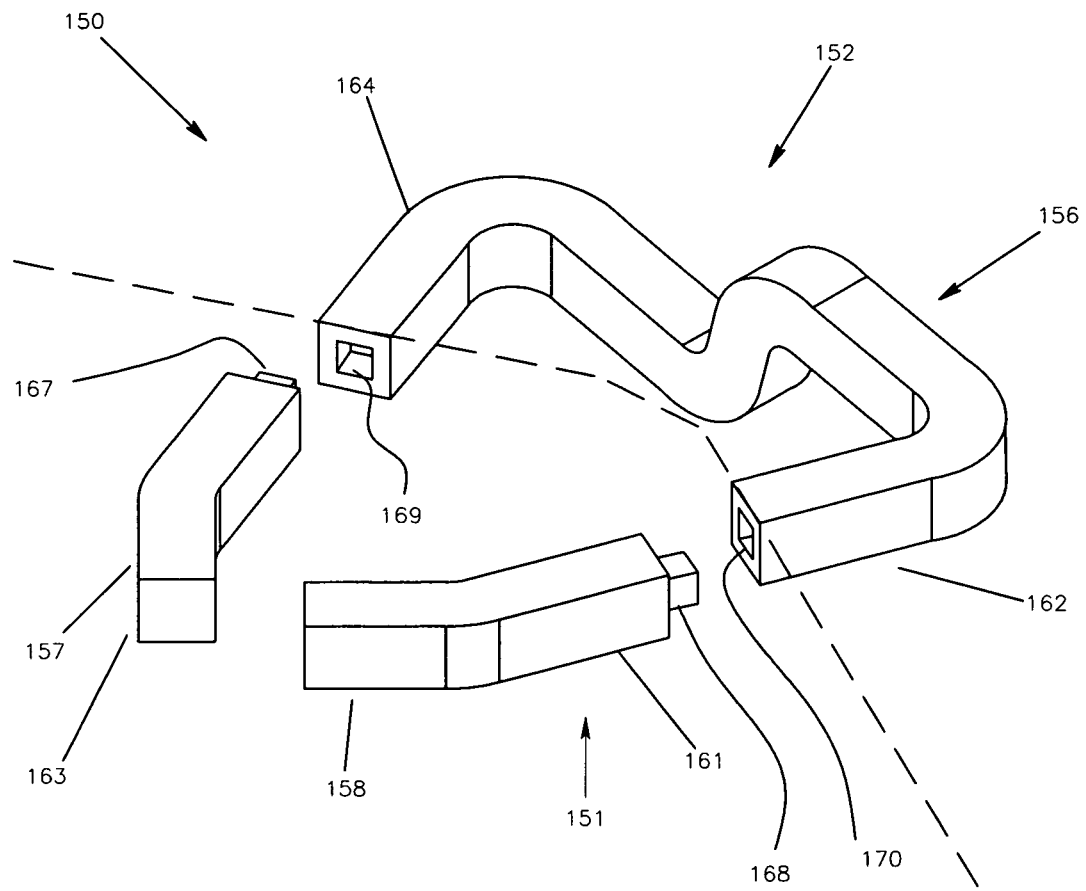
FIG. 5C provides a perspective view of a shape-memory device manufactured from separate components according to an alternative first embodiment.

Alternatively, a shape-memory device 150 similar in shape and function to the shape-memory device 100 may be formed utilizing multiple components, wherein the shape-memory device 150 moves from a second shape to a first shape upon the application of activation energy. As shown in FIG. 5C, the shape-memory device 150 includes a bridge 156, a first leg 157, and a second leg 158. The first leg 157 includes an upper segment 164 and a separate lower segment 163 that includes an end that contracts inward when activation energy is applied, and the second leg 158 includes an upper segment 162 and a separate lower segment 161 that includes an end that contracts inward when activation energy is applied. The shape-memory device 150 further includes a first portion 151 and a second portion 152 that have different transition temperatures.

In this alternative embodiment, the interface between the first portion 151 and the second portion 152 similarly passes through a mid portion of the first and second legs 157-158. A free end of the upper segment 164 includes a recess 169, and a free end of the upper segment 162 includes a recess 170. The lower segment 163 includes a first protrusion 167 and the lower segment 161 includes a second protrusion 168. The first portion 151 includes the lower segments 163 and 161, and the second portion 152 includes the bridge 156 and the upper segments 162 and 164.

In this alternative embodiment, the lower segments 161 and 163 are formed at a first transition temperature and the bridge 156 and upper segments 162 and 164 are formed at a second transition temperature. The lower segments 161 and 163 are then assembled together with the upper segments 162 and the bridge 156 to create the composite shape-memory device 150. In this specific example, the protrusions 167-168 are complementary in shape to the recesses 169-170, and of a size suitable for being press fit into a respective recess 169 or 170. Illustratively, the first protrusion 167 is press fit into the recess 169, and the second protrusion 168 is press fit into the recess 170, such that the contracting ends contract toward each other when moving from the second shape to the first shape, in similar fashion to the first embodiment.

Figure 5D:
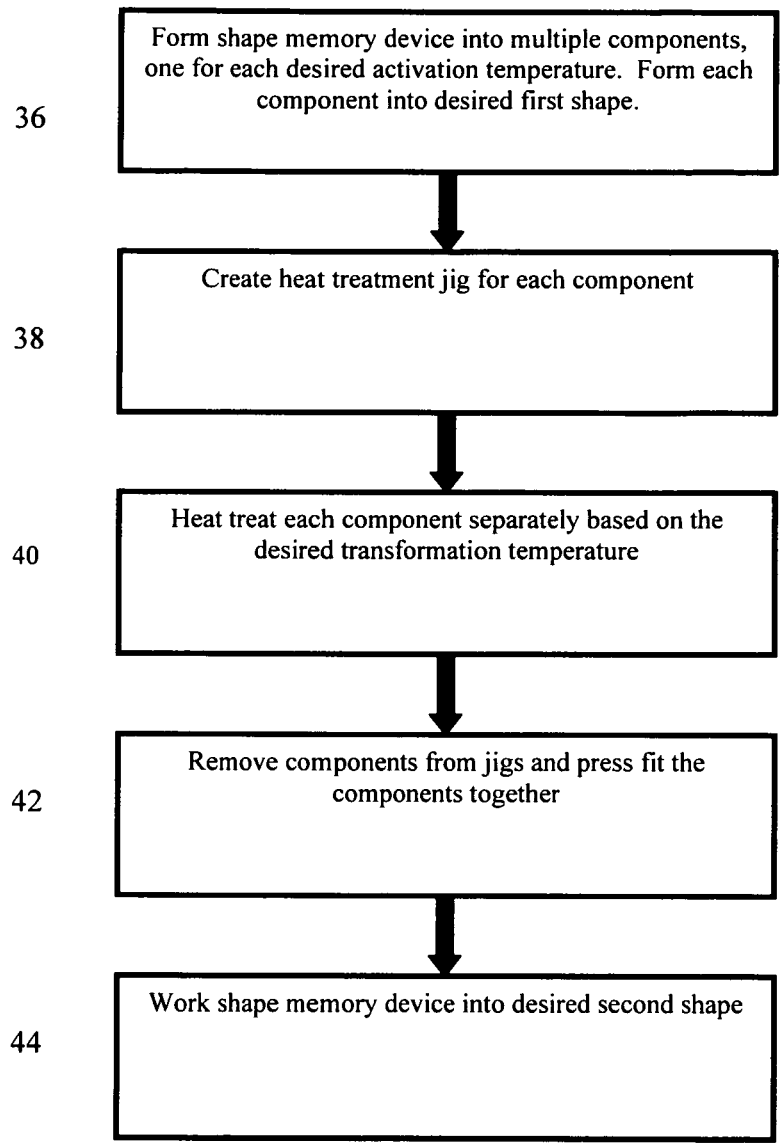
FIG. 5D provides a flowchart illustrating the method steps for manufacturing the shape-memory device according to the alternative first embodiment.

FIG. 5D provides a flowchart illustrating the method steps for manufacturing the shape-memory device 150 according to this invention. The manufacturing process commences with step 36, wherein a shape-memory device is split into multiple components, each having a desired activation temperature. Each component is formed in the respective first shape. The process continues with step 38, wherein a heat treatment jig is created for each component. Step 40 provides for separately heat-treating each component to achieve the desired transformation temperature. Next, the components are removed from the heat-treating jigs and assembled together using any suitable process, step 42. In this specific example, the different components are press fit together, however, one of ordinary skill in the art will recognize that virtually any form of attachment may be utilized, provided that adequate restraining forces are achieved. The shape-memory device 150 is then worked into the respective second shapes, step 44.

As the assembled shape-memory device 150 is now a single unit, use of the shape-memory device 150 is substantially identical to the shape-memory device 100. Accordingly, the methods provided in FIGS. 4A-4D are applicable to the shape-memory device 150, and will therefore not be further described.

While this specific example has been shown with separate components being press fit together, one of ordinary skill in the art will recognize that virtually any form of mechanical attaching scheme may be utilized if it provides adequate results, including welding, mechanical fasteners, and the like. One of ordinary skill in the art will further recognize that the changing of the interface between the first portion 151 and the second portion 152 to a plane parallel to the cross section is for design and manufacturing simplification purposes.

Figures 6A, 6B:
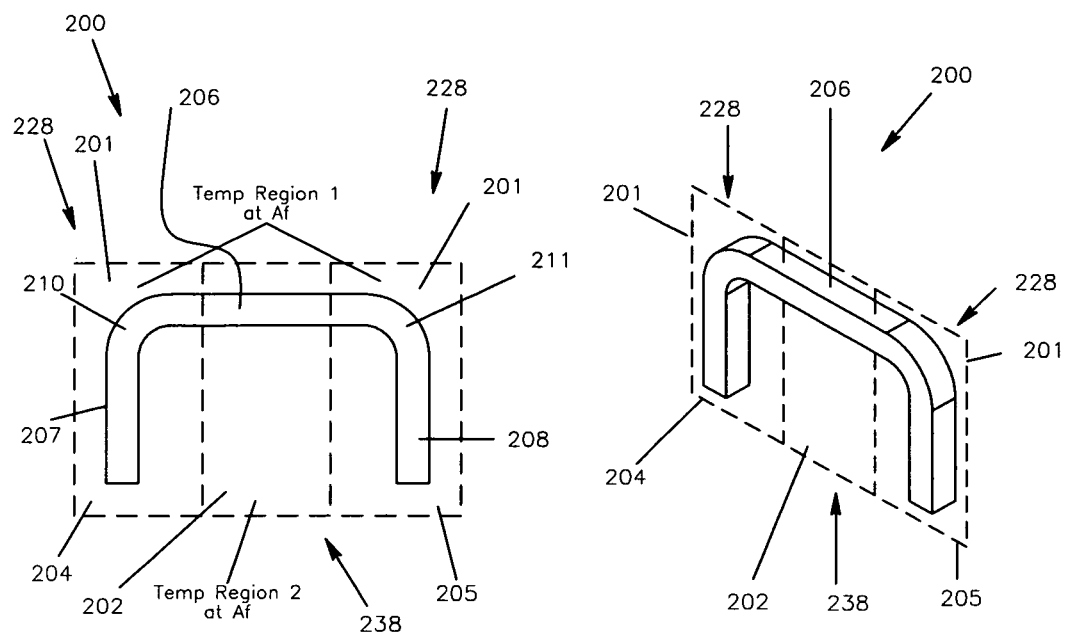
FIG. 6A provides a frontal view of a shape-memory device including multiple transition temperatures according to a second embodiment.
FIG. 6B provides a perspective view of the shape-memory device including multiple transition temperatures according to the second embodiment.
Figure 7A:
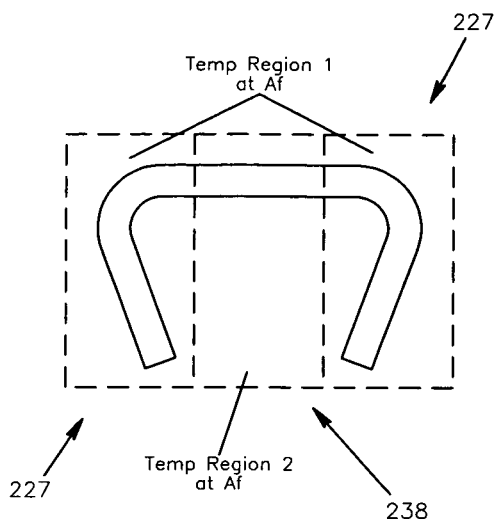
FIG. 7A provides a frontal view of the shape-memory device after a first transition temperature has been activated according to the second embodiment.
Figure 7B:
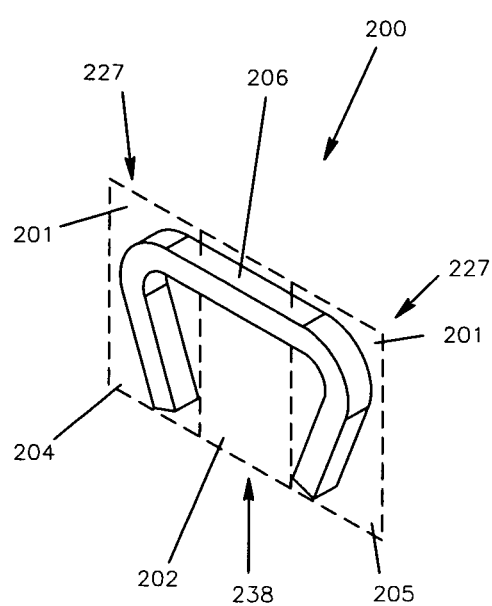
FIG. 7B provides a perspective view of the shape-memory device after the first transition temperature has been activated according to the second embodiment.

In a second embodiment, a shape-memory device 200 includes a first portion 201 having multiple zones, and a second portion 202 having a single zone. As shown in FIG. 6A, the first portion 201 includes a first zone 204 and a second zone 205 that have a first shape 227 and a second shape 228, and a first transition temperature. The second shape 228 is shown in FIGS. 6A-6B while the first shape 227 is shown in FIGS. 7A-7B. The second portion 202 includes a second shape 238, shown in FIGS. 7A-7B, and a first shape 237, shown in FIGS. 8A-8B, and a second transition temperature. In this example, the shape-memory device 200 is a staple that may be utilized as a surgical implant, and includes a first leg 207, a second leg 208, a bridge 206, a first bend 210, and a second bend 211.

In this second embodiment, the first bend 210 is disposed between the first leg 207 and the bridge 206, and the second bend 211 is disposed between the second leg 208 and the bridge 206. The first bend 210 and the second bend 211 contract inward upon the application of activation energy, such that the ends of the legs 207-208 are closer together in the first shape 227.

The first zone 204 of the first portion 201 encompasses the first leg 207 and the first bend 210, and the second zone 205 of the first portion 201 encompasses the second leg 208 and the second bend 211. As the first zone 204 and the second zone 205 of the first portion 201 have the same transition temperature, the first bend 210 and the second bend 211 transition from the second shape 228 to the first shape 227 substantially symmetrically, and at the same time, as shown in FIGS. 7A-7B. In this specific example, the bends 210-211 contract inward approximately thirty degrees. While this example has been shown with a contraction of approximately thirty degrees, one of ordinary skill in the art will recognize that virtually any angle of contraction may be utilized, dependent upon the limits of shape-memory materials.

Figure 8A:
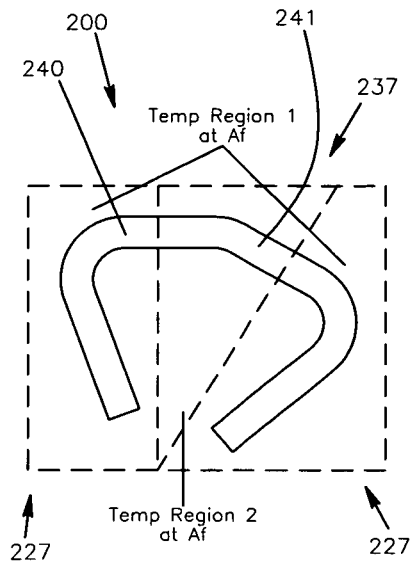
FIG. 8A provides a frontal view of the shape-memory device after the first transition temperature and a second transition temperature have been activated according to the second embodiment.
Figure 8B:
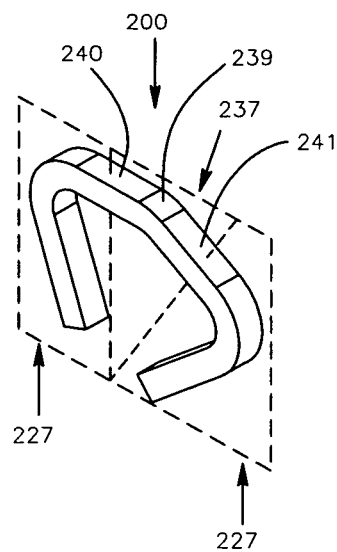
FIG. 8B provides a perspective view of the shape-memory device after the first transition temperature and the second transition temperature have been activated according to the second embodiment.

The second portion 202 encompasses the bridge 206, and is disposed between the first and second bends 210-211. In this second embodiment, the bridge 206 includes a transition member 239. As shown in FIGS. 8A-8B, the bridge 206 includes a first member 240, a second member 241, and the transition member 239 disposed between the first and second members 240-241. In this specific example, the transition member 239 is a bend having a midpoint. The first member 240 is connected to the first bend 210, and the second member 241 is connected to the second bend 211. In the second shape 238, the transition member 239 spans approximately one hundred and eighty degrees, thereby placing the first and second members 240-241 substantially collinear. Upon the application of activation energy, the transition member 239 contracts inward, thereby moving the ends of the legs 207-208 closer. In the first shape 237, the transition member 239 is disposed at approximately thirty degrees, however, one of ordinary skill in the art will recognize that virtually any bend angle may be utilized, dependent upon the limitation of shape-memory materials, and shape-memory device designs.

Figure 9A:
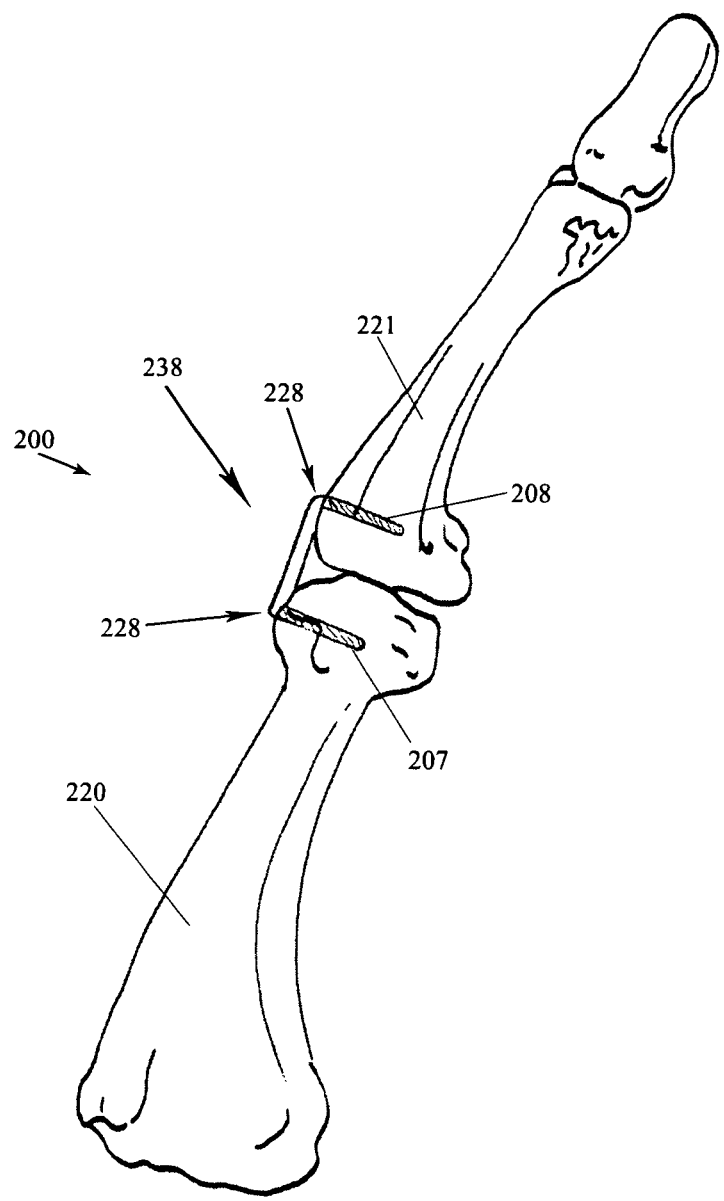
FIG. 9A provides a frontal view of the shape-memory device in use according to the second embodiment.
Figure 9B:
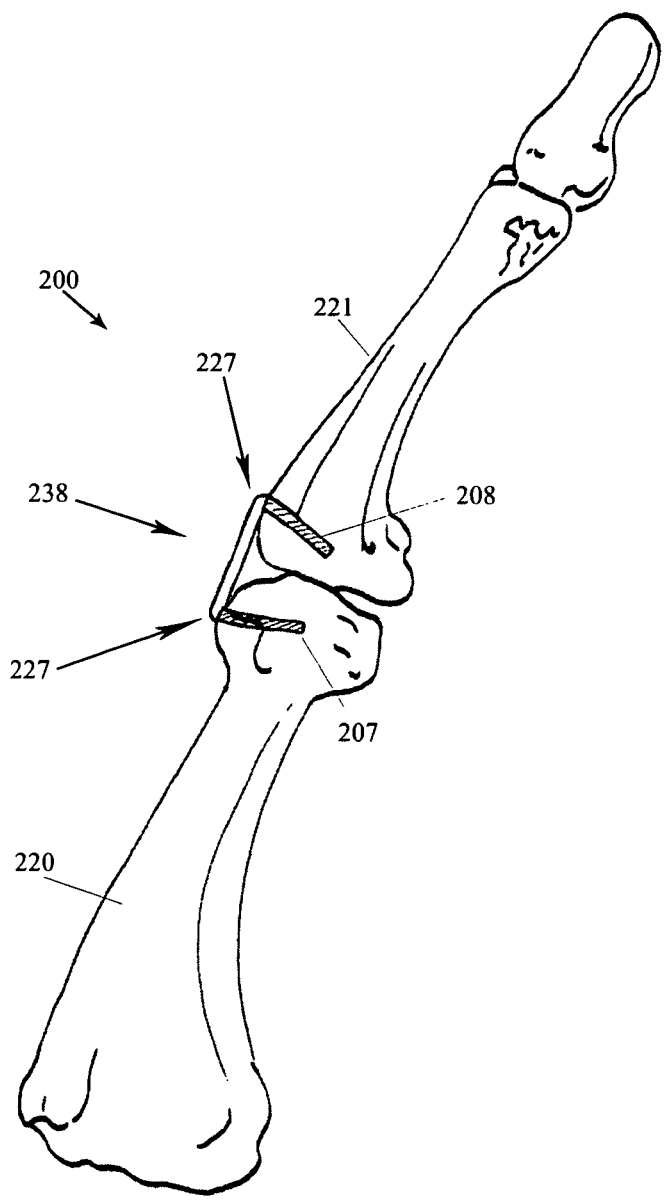
FIG. 9B provides a frontal view of the shape-memory device after the first portion is activated according to the second embodiment.
Figure 9C:
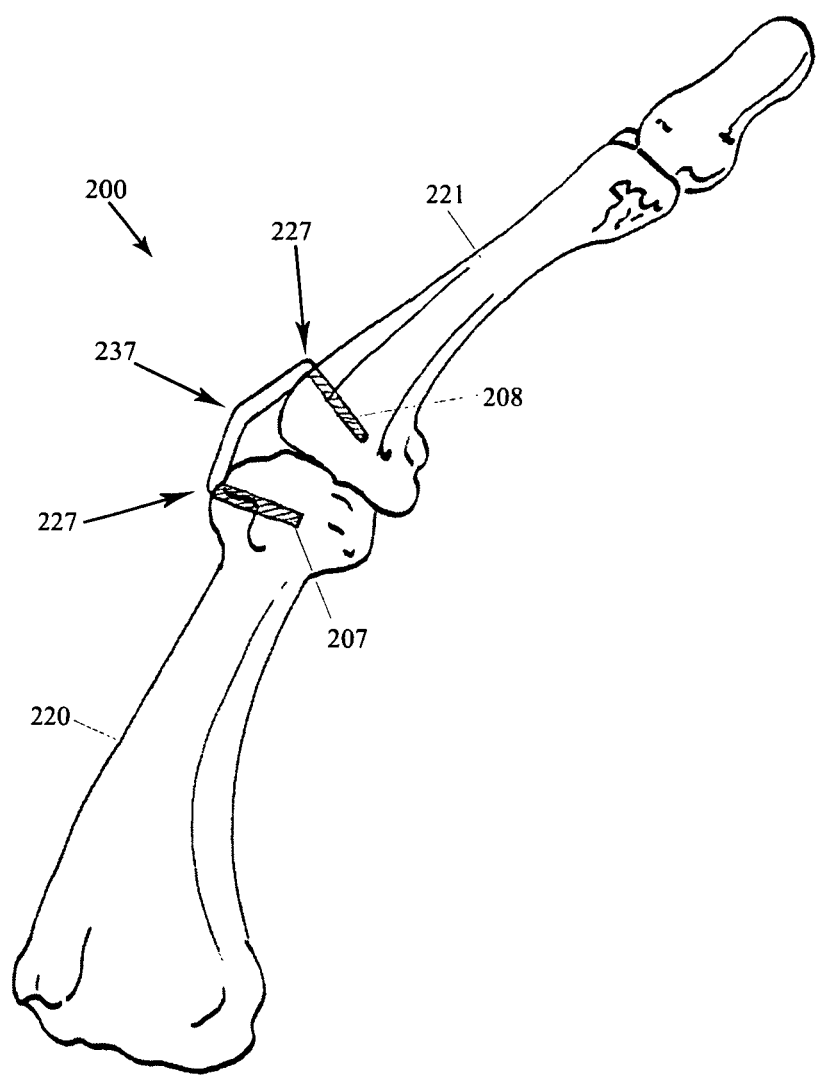
FIG. 9C provides a frontal view of the shape-memory device after the first and second portions have been activated according to the second embodiment.

In use, the shape-memory device 200 substantially follows the method flowchart provided in FIG. 4A, wherein the shape-memory device 200 is placed into a desired working position. In this example, the desired working position is shown in FIG. 9A, and provides for the first leg 207 of the shape-memory device 200 to be installed onto a first bone 220 and an adjacent second bone 221. With both portions 201 and 202 in their respective second shapes 228 and 238, the first leg 220 is inserted into the first bone 220, and the second leg 208 inserted into the second bone 221. As shown in step 12 of FIG. 4A, the surgeon initiates a first desired shape transformation by delivering activation energy to the first and second zones 204-205 of the first portion 201, thereby forcing the transformation of the first and second bends 210-211 from the second shape 228 to the first shape 227 and drawing the first and second bones 220-221 toward each other, as shown in FIG. 9B. Alternatively, body heat may be utilized as activation energy for the first portion 201. The surgeon then moves to step 14, wherein the surgeon initiates a second desired shape transformation by applying activation energy to the second portion 202. Upon the application of activation energy to the second portion 202, the transition member 239 contracts, thereby rotating the second bone 221 relative to the first bone 220, as shown in FIG. 9C. Alternatively, if body heat is not utilized as activation energy for the first portion 201, body heat may be utilized as activation energy for the second portion 202. Illustratively, in this example, the second bone 221 rotates approximately thirty degrees relative to the first bone 220 to reach the first shape 237 of the second portion 202. One of ordinary skill in the art will recognize that the second portion 202 may be contracted to any angle up to and including the thirty degrees shown.

Figure 8C:
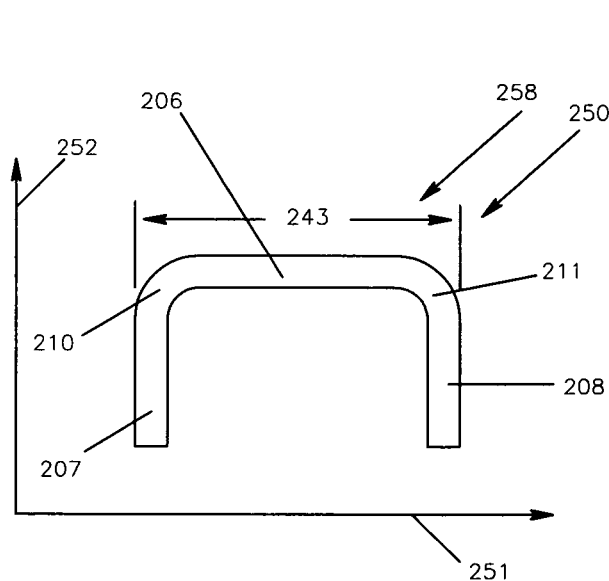
FIG. 8C provides a front view of a shape-memory device having only one transition temperature according to an extension of the second embodiment.
Figure 8D:
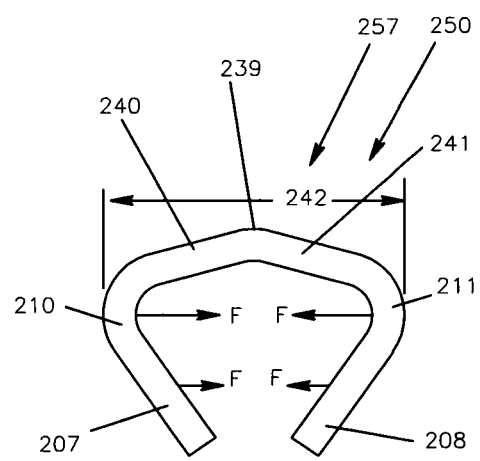
FIG. 8D provides a front view of the shape-memory device after the first transition temperature has been activated according to the extension of the second embodiment.

In an extension of the second embodiment, the shape-memory device 200 shown as a multiple activation temperature shape-memory device may also be formed as a single transition temperature shape-memory device 250. In this alternative embodiment, the structure of the shape-memory device 250 is substantially identical to the shape-memory device 200, and therefore has been labeled with like numerals. As shown in FIGS. 8C and 8D, the shape-memory device 250 includes only a single portion, and therefore has only one transition temperature.

In a first shape 257, the first and second members 240-241 of the bridge 206 are disposed at an angle of approximately thirty degrees, and the legs 207-208 are disposed at an angle of approximately sixty degrees from a connecting first or second member 240 or 241. While this extension of the second embodiment has been shown with the legs 207-208 and the first and second members 240-241 disposed at approximately sixty degrees from the bridge 206 components, one of ordinary skill in the art will recognize that virtually any bend angle and bend direction may be utilized, dependent upon the limitation of shape-memory materials, and shape-memory device designs.

In a second shape 258, the first and second legs 207-208 are disposed substantially perpendicular to the bridge 206 components, and the first and second members 240-241 are substantially planar. As shown in FIG. 8C, the bridge 206 is substantially parallel to a horizontal axis 251 and the legs 207-208 are substantially parallel to a vertical axis 252. One of ordinary skill in the art will recognize that virtually any bend angle may be utilized for a second shape, dependent upon the limitation of shape-memory materials, and shape-memory device designs.

Upon the application of activation energy, all shape-changing components of the shape-memory device 250 transition from the second shape 258 to the first shape 257 substantially simultaneously. Use of the shape-memory device 250 is similar to the shape-memory device 200, wherein the legs 207-208 restrain the shape-changing bridge 206 to first and second bones, and the bridge 206 reorients the first and second bones when the bridge 206 shape-changes.

The transition from the second shape 258 to the first shape 257 occurs with recognizable force. As shown in FIG. 8D, a force is created between the legs 207-208 when the bends 210-211 contract. Additionally, a force is created between the legs 207-208 when the transition member 239 contracts, as an effective bridge length decreases when moving from the second shape 258 to the first shape 257. Illustratively, a bridge length 243 for the second shape 258 is longer than a bridge length 242 for the first shape 257, thereby creating compressive forces between the legs 207-208 as the bridge 206 contracts.

While this embodiment has been shown with the transition member 239 as a bend, one of ordinary skill in the art will recognize that virtually any form of transition member may be utilized to provide varied results. One of ordinary skill in the art will further recognize that the transition member 239 and the bends 210-211 may contract or expand dependent upon desired results.

Figure 10A:
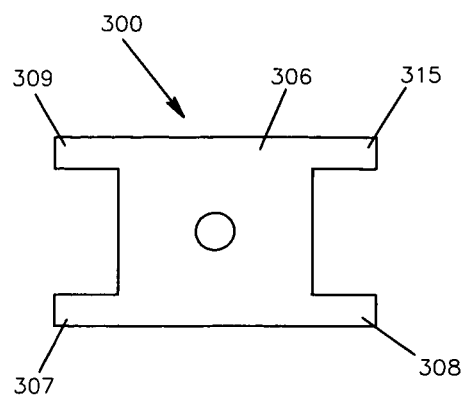
FIG. 10A provides a top view of a shape-memory device according to a third embodiment.
Figure 10B:
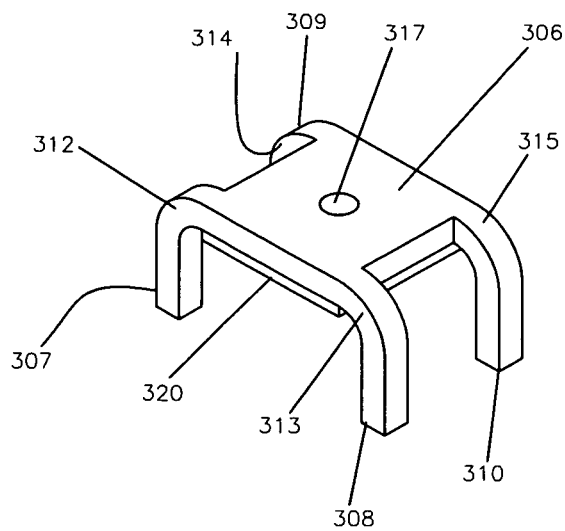
FIG. 10B provides a perspective view of the shape-memory device according to the third embodiment.
Figure 10C:
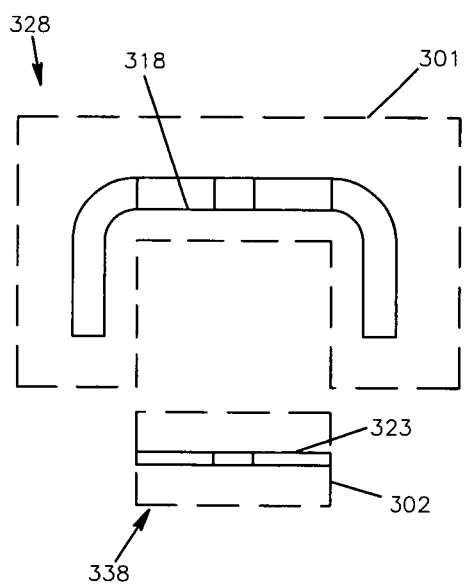
FIG. 10C provides an exploded view of the shape-memory device according to the third embodiment.
Figure 10D:
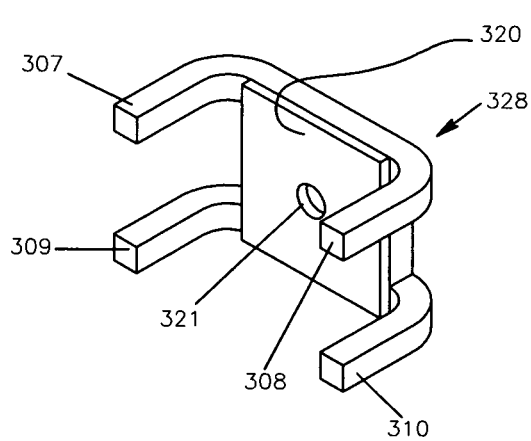
FIG. 10D provides a second perspective view of the shape-memory device according to the third embodiment.
Figure 11A:
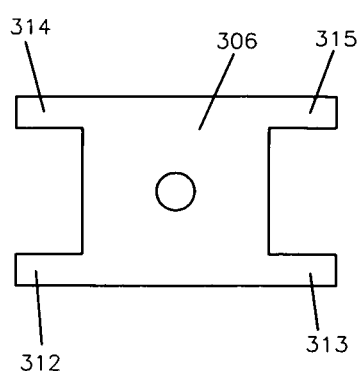
FIG. 11A provides a top view of the shape-memory device after a first portion has been activated according to the third embodiment.
Figure 11B:
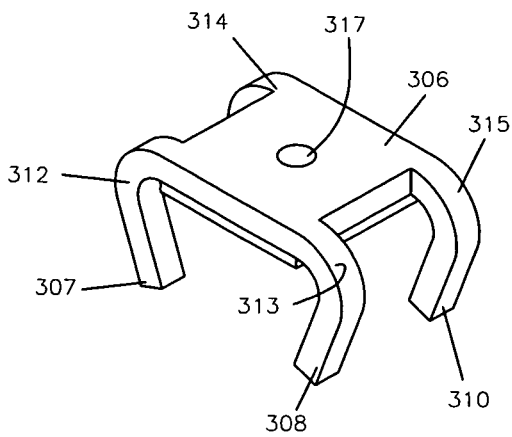
FIG. 11B provides a perspective view of the shape-memory device after a first portion has been activated according to the third embodiment.
Figure 11C:
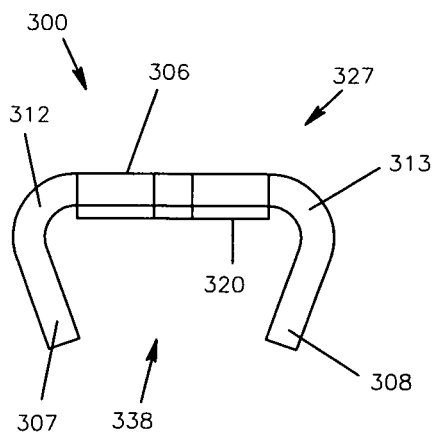
FIG. 11C provides a frontal view of the shape-memory device after a first portion has been activated according to the third embodiment.
Figure 11D:
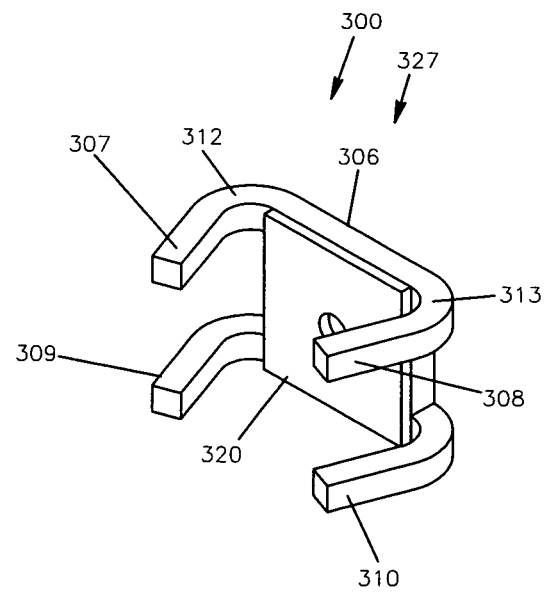
FIG. 11D provides a second perspective view of the shape-memory device after a first portion has been activated according to the third embodiment.
Figure 12A:
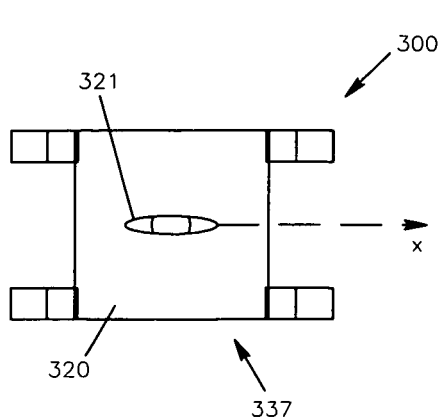
FIG. 12A provides a top view of the shape-memory device after the first and second portions has been activated according to the third embodiment.
Figure 12B:
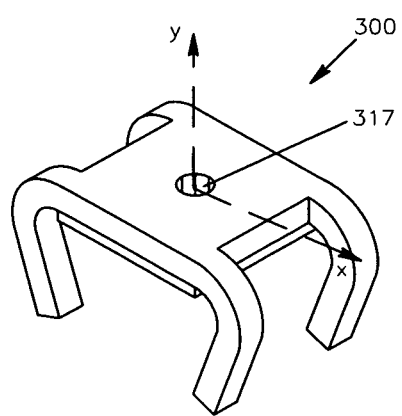
FIG. 12B provides a perspective view of the shape-memory device after the first and second portions have been activated according to the third embodiment.
Figure 12C:
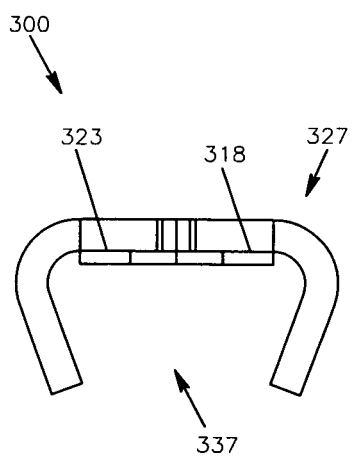
FIG. 12C provides a frontal view of the shape-memory device after the first and second portions have been activated according to the third embodiment.

In a third embodiment, a shape-memory device 300 is formed utilizing layers. As shown in FIGS. 10A-10D, the shape-memory device 300 includes a first portion 301 having a first transition temperature, a first shape 327, and a second shape 328, and a second portion 302 having a second transition temperature, a first shape 337, and a second shape 338. In this third embodiment, the portions 301 and 302 are disposed in layers. The first shape 327 is shown in FIG. 11C-11C, and the first shape 337 is shown in FIG. 12A.

The first portion 301 includes a bridge 306, first through fourth legs 307-310, and first through fourth bends 312-315. In this specific example, the bridge 306 is planar and includes a mounting surface 318 and an aperture 317. The first and third legs 307 and 309 are disposed on a single end of the bridge 306, and the second and fourth legs 308 and 310 are symmetrically disposed on an opposite end of the bridge 306. The first through fourth bends 312-315 are disposed between the first through fourth legs 307-310, respectively, and the bridge 306, as shown in FIG. 10B.

In the second shape 328, the legs 307-310 are disposed substantially perpendicular to the bridge 306, such that the bends 312-315 span approximately ninety degrees. Upon the application of heat energy to the first portion 301, the bends 312-315 contract approximately thirty degrees, such that the legs 307-310 are disposed at approximately sixty degrees relative to the bridge 306 in the first shape 327, as shown in FIGS. 11A-11D.

The second portion 302 includes a plate 320 having a contraction feature, and is of a size complementary to the bridge 306 of the first portion 301. In this specific example the contraction feature is a collapsing aperture 321. A mating surface 323 of the plate 320 is disposed on the mounting surface 318 of the bridge 306, such that the collapsing aperture 321 is in alignment with the aperture 317 of the bridge 306. The plate 320 may be secured to the bridge 306 utilizing any suitable means known in the art, including welding, press-fitting, adhesives, and the like. While the contraction feature of this example has been shown as a collapsing aperture 321, one of ordinary skill in the art will recognize that virtually any form of contraction or expansion feature may be utilized to deliver forcible displacement.

Figure 12D:
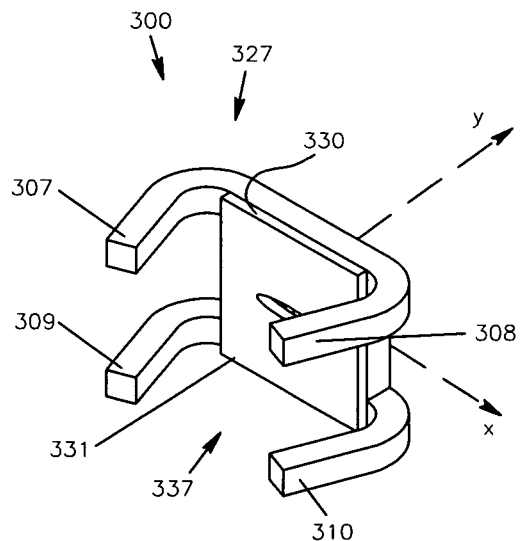
FIG. 12D provides a second perspective view of the shape-memory device after the first and second portions have been activated according to the third embodiment.

In the second shape 338, the plate 320 is planar and the collapsing aperture 321 is at a full-round position. In the first shape 337, plate 320 maintains the planar form, however, the collapsing aperture 321 collapses through the aperture, thereby drawing a first end 330 and a second end 331 of the plate 320 closer. In this specific example, the contraction feature collapses to an X-Y plane, as shown in FIG. 12D. While this embodiment has been shown with the collapsing aperture 321 collapsing through the plane X-Y, one of ordinary skill in the art will recognize the virtually any plane may be selected as a collapse plane, dependent upon desired contractions.

Upon appropriate attachment of the plate 320 to the bridge 306, the shape-memory device 300 has multiple portions having different transition temperatures, as disclosed in the previous embodiments, and therefore follows the method flowchart of FIG. 4A. As shown in step 10, the shape-memory device 300, in the second shapes 328 and 338, is placed into a desired working position. Once installed, the user may initiate a first desired transformation, step 12. In this specific example, the user provides activation energy to the first portion 301, to move the first portion 301 from the second shape 328 to the first shape 327, thereby contracting the bends 312-315 and bringing the ends of the legs 307-310 closer together. Step 14 provides for initiating a second desired transformation of a second transition temperature. As shown in FIGS. 12A-12D, the user delivers activation energy to the second portion 302 to move the plate 320 from the second shape 338 to the first shape 337, thereby contracting the collapsing aperture 321, and providing compressive forces between the first and third legs 307 and 309, and between the second and fourth legs 308 and 310.

Manufacturing of the shape-memory device 300 that includes multiple layers for independent activation requires the separate formation of each layer in the respective first shape, independent heat treatment to create a shape-memory profile, and bonding of the layers together. Illustratively, in this third embodiment the first portion 301 and the second portion 302 are welded together along the outer edges. As previously disclosed, each layer includes a first shape and a second shape, and may be worked from the first shapes to second shapes, thereby creating the ability to move from the second shape to the first shape upon the application of activation energy. While this shape-memory device 300 has been shown with the first portion 301 and the second portion 302 welded together, one of ordinary skill in the art will recognize that any form of suitable connection may be utilized to bond the layers to one another, including mechanical fasteners, adhesive bonds, and the like.

Figure 13:
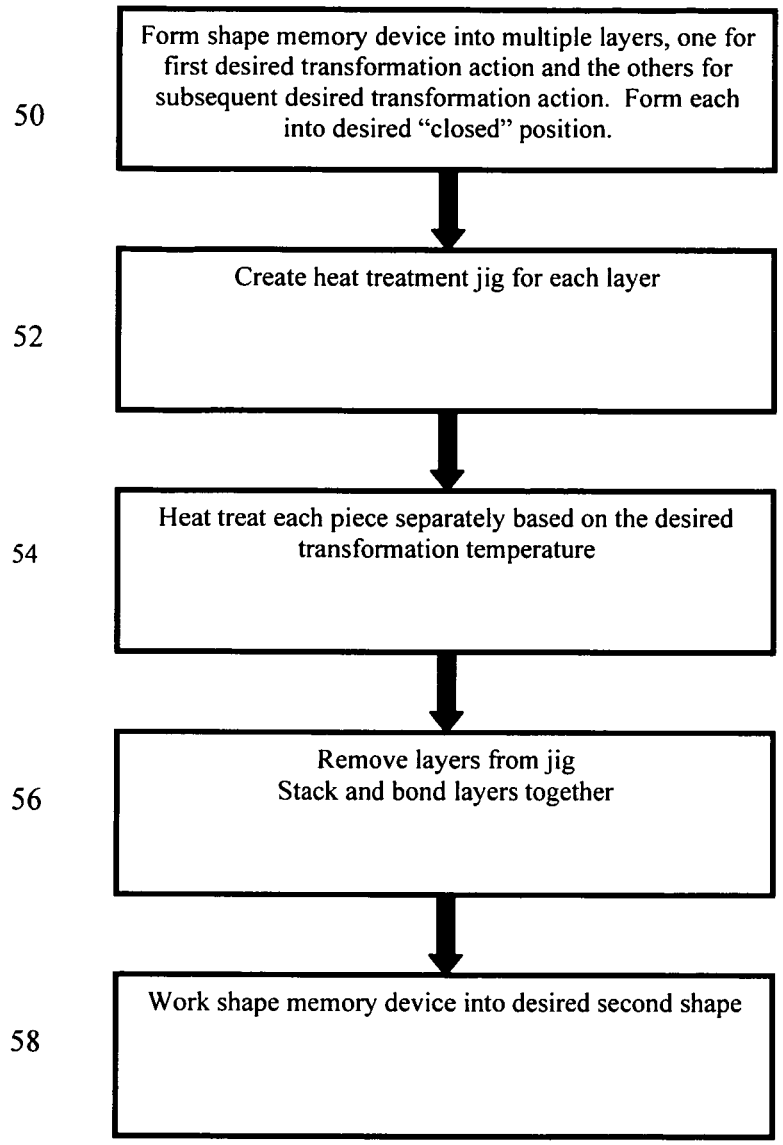
FIG. 13 provides a flowchart illustrating the method steps of manufacturing the shape-memory device according to the third embodiment.

As shown in the method flowchart of FIG. 13, the process for manufacturing the shape-memory device commences with step 50, wherein the shape-memory device 300 is formed into the first portion 301 that delivers a first desired transformation action and the second portion 302 that delivers a second desired transformation action. In this specific example of the manufacturing process, the first portion 301 is formed in the first shape 327, and the second portion 302 is formed in the first shape 337. The process then requires the creation of a heat treatment jig for each layer, step 52. Step 54 provides for heat treating each layer separately based on the desired transformation temperature. As previously disclosed, heat treatment processes may be altered through both duration and temperature of the heat treatment. Upon completion of the heat treatments, the layers are removed from the jigs, stacked and bonded together to create the shape-memory device 300 in the first shapes 327 and 337, step 56. After bonding, the first and second portions 301 and 302 of the shape-memory device 300 are worked into the second shapes 328 and 338, step 58. As such, activation energy may be delivered to first portion 301 or the second portion 302 to cause a desired transformation action.

While this embodiment has been shown with two distinct layers, one of ordinary skill in the art will readily recognize that virtually any number of layers may be utilized. One of ordinary skill in the art will further recognize that the use of individual layers having different transition temperatures does not preclude the use of layers having multiple transition temperatures as described in the previous embodiments.

Figure 14A:
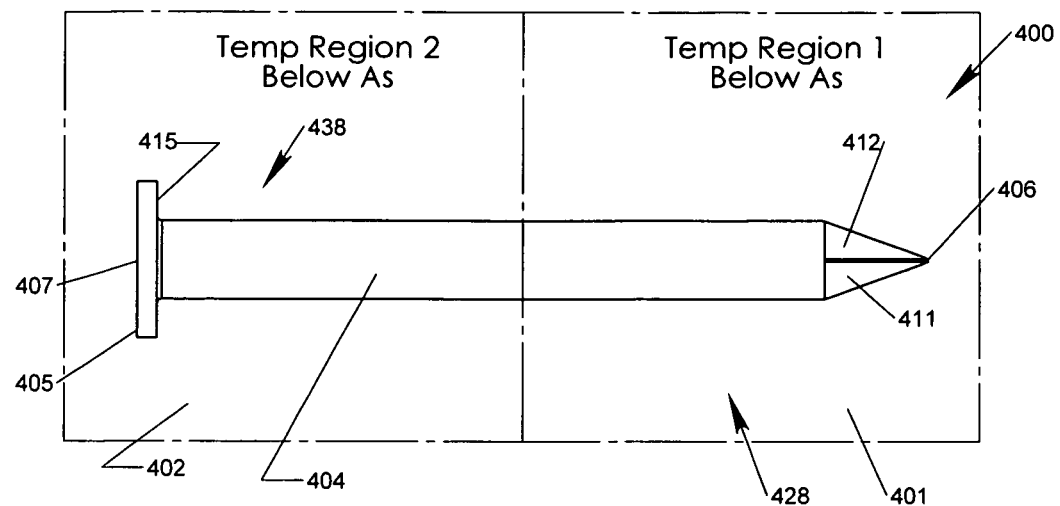
FIG. 14A provides a frontal view of a shape-memory device including multiple transition temperatures according to a fourth embodiment.
Figure 14B:
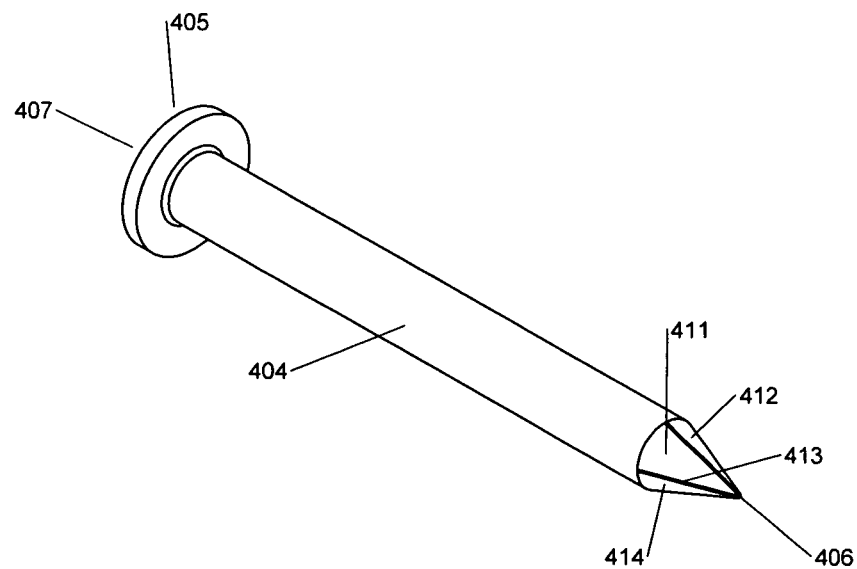
FIG. 14B provides a perspective view of the shape-memory device including multiple transition temperatures according to the fourth embodiment.

In a fourth embodiment, a shape-memory device 400 includes a first portion 401 having a first transition temperature, and a second portion 402 having a second transition temperature. In this example, the shape-memory device 400 is a pin, and includes a body 404 having a first end 406, a second end 407, and a flange 405. As shown in FIGS. 14A-14B, the first portion 401 and the second portion 402 meet substantially at a midpoint of the shape-memory device 400.

The first portion 401 encompasses the first end 406, and includes a first shape 427 and a second shape 428. The first end 406 includes a first through fourth prongs 411-414. In the second shape 428 the first through fourth prongs 411-414 are adjacent to each other, such that the first end 406 is pointed. In the first shape 427, shown in FIG. 15A-15B, the first through fourth prongs 411-414 are disposed at an angle relative to the body 404. Illustratively, in this fourth embodiment, the prongs 411-414 are disposed at an angle of approximately thirty degrees relative to the axis of the cylindrical body 404.

The second portion 402 encompasses the second end 407 and the flange 405, and includes a first shape 437 and a second shape 438. In the second shape 438 the flange 405 includes a planar face 415. The planar face 415 is disposed on the second end 407 of the body 404. In the first shape 437, shown in FIG. 16A-16B, the planar face 415 extends toward the first end 406, substantially parallel to the axis of the cylindrical body 404, thereby shortening the distance between the planar face 415 and the first through fourth prongs 411-414.

While this embodiment has been shown with the shape-memory device 400 having two portions 401 and 402 moving from the second shapes 428 and 438 to the first shapes 427 and 437, respectively, it should be apparent that both portions 401 and 402 are usable at virtually any point along the transition between the second shapes 428 and 438 and the first shapes 427 and 437, respectively. Accordingly, an end-use shape may designate any shape between the second shapes 428 and 438 and up to and including the first shapes 427 and 437, respectively. The amount of heat energy applied to the deformed shape determines the amount of transition from the second shapes 428 and 438 to the first shapes 427 and 437, respectively.

Figure 15A:
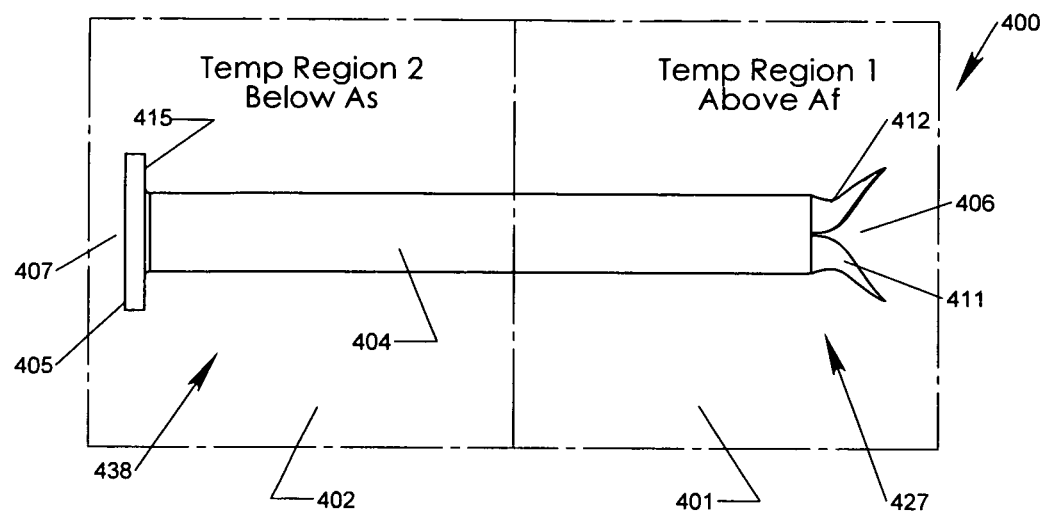
FIG. 15A provides a frontal view of a shape-memory device including multiple transition temperatures after a first portion has been activated according to the fourth embodiment.
Figure 15B:
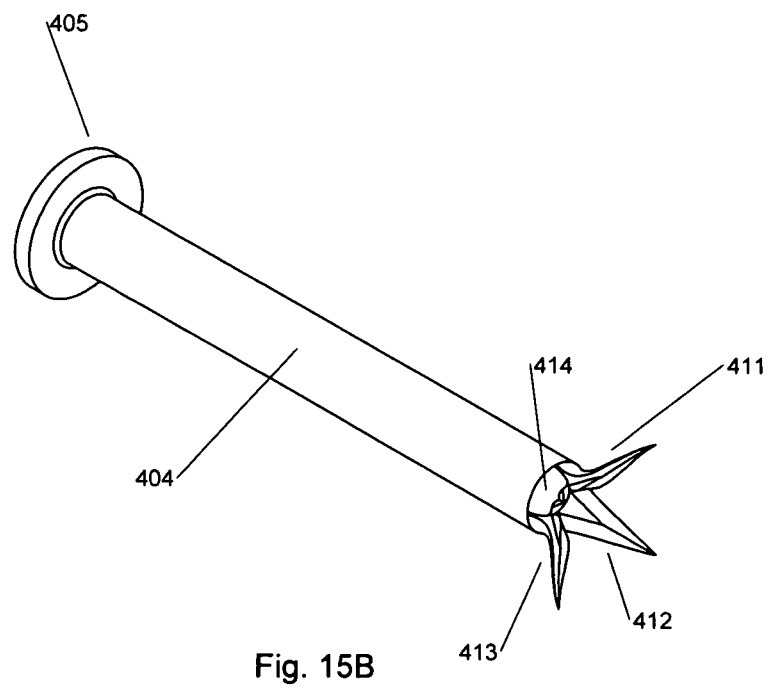
FIG. 15B provides a perspective view of the shape-memory device including multiple transition temperatures after the first portion has been activated according to the fourth embodiment.

As shown in FIG. 14A, both the first portion 401 and the second portion 402 of the shape-memory device 400 are disposed in the second shapes 428 and 438, at temperatures below the commencement point for Austenite to form ($A_s$). FIG. 15A provides an illustration of the shape-memory device 400 after heat energy has been applied to the first portion 401. At this point, the temperature of the first portion 401 has been raised, and the entire first portion 401 has been converted to Austenite at temperature $A_F$-First Portion. Accordingly, the first portion 401 has fully transitioned to the first shape 427, wherein the prongs 411-414 extend outward.

As shown in FIG. 15A, the second portion 402 remains in the second shape 438, because the transition temperature for the second portion 402 is higher than the transition temperature for the first portion 401.

Figure 16A:
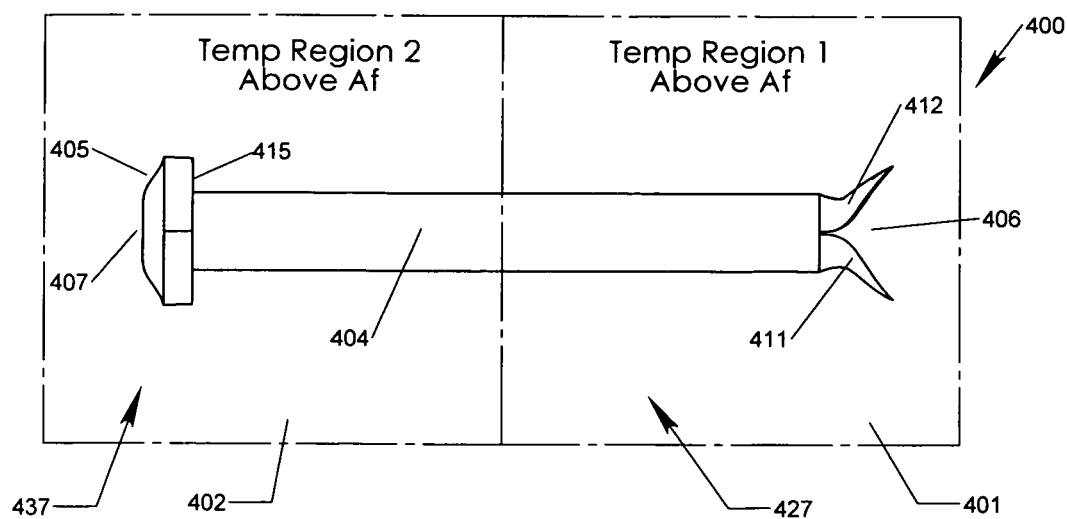
FIG. 16A provides a frontal view of a shape-memory device including multiple transition temperatures after the first and second portions have been activated according to the fourth embodiment.
Figure 16B:
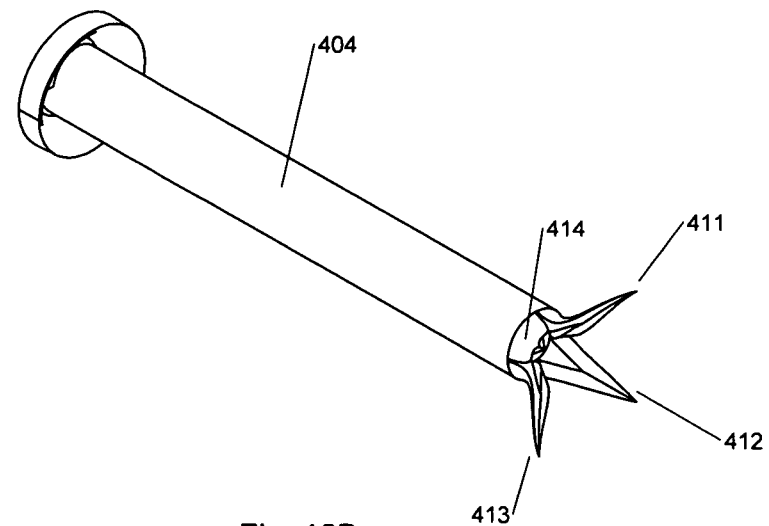
FIG. 16B provides a perspective view of the shape-memory device including multiple transition temperatures after the first and second portions has been activated according to the fourth embodiment.

Upon the continued application of heat energy to the shape-memory device 400 to the $A_s$-Second Portion temperature, the second portion 402 commences to shape change, and continues to shape change until the $A_F$-Second Portion temperature is reached, at which point the flange 405 has fully contracted to the first shape 437, as shown in FIGS. 16A-16B.

Use of the shape-memory device 400 having multiple activation temperatures follows the flowchart illustrated in FIG. 4A. The process commences with the placement of the shape-memory device 400 into a desired position, step 10. Illustratively, the shape-memory device 400 may be placed into a hole. The operator must then deliver activation energy to raise the temperature of a first portion 401 to at least temperature $A_F$-First Portion, thereby forcing the first portion 401 of the shape-memory device 400 to move from the second shape 428 to the first shape 427, step 12. In this specific example, the prongs 411-414 extend outward, thereby securing the shape-memory device 400 in the hole. The operator then delivers adequate heat energy to the second portion 402 of the shape-memory device 400 to reach $A_F$-Second Portion, at which point the second portion 402 has shape changed from the second shape 438 to the first shape 437, step 14. In this example, the flange 405 extends toward the first end 406 in a direction substantially parallel to the axis of the cylindrical body 404. At that point, both transition temperatures have been reached.

The shape-memory device 400 may be utilized as an implant in a living body in similar fashion to the first embodiment, and therefore follows the flowchart of FIG. 4A. As described in the flowchart of FIG. 4A, a surgeon has the flexibility to initiate the desired transformations in virtually any order, dependent upon site specific conditions and desired results. Accordingly, the surgeon may repeatedly deliver activation energy to a first or second portion 401 or 402 to effect a desired change.

In an alternative embodiment, a shape-memory device 500 includes a first portion 501 having no transition temperature, and a second portion 502 having a transition temperature, as shown in FIGS. 17A-17C. The first portion 501 may be formed from a shape-memory material that is at a pure Austenite state or a pure Martensite state.

In this specific example of the shape-memory device 500 the second portion 502 includes multiple zones, a first shape 537 shown in FIG. 19C, and a second shape 538, shown in FIG. 17A-B. Illustratively, the shape-memory device 500 is a staple that includes a bridge 506, first through fourth legs 507-510, and first through fourth bends 512-515. The first and third legs 507 and 509 are disposed on a same side of the bridge 506, and the second and fourth legs 508 and 510 are symmetrically disposed on an opposite end. In this example, the first bend 512 is disposed between the first leg 507 and the bridge 506, the second bend 513 is disposed between the second leg 508 and the bridge 506, the third bend 514 is disposed between the third leg 509 and the bridge 506, and the fourth bend 515 is disposed between the fourth leg 510 and the bridge 506.

Figure 18A:
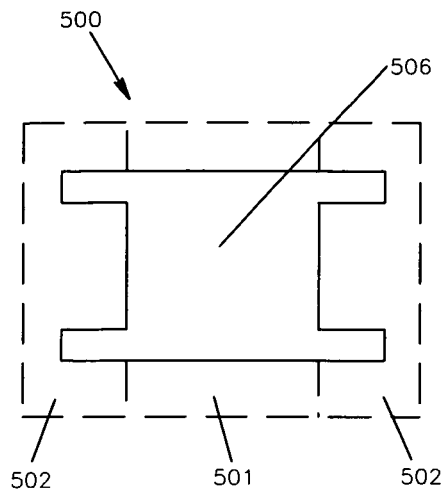
FIG. 18A provides a top view of a shape-memory device including the single transition temperature and the permanently formed section after forming the formed section according to the fifth embodiment.
Figure 18B:
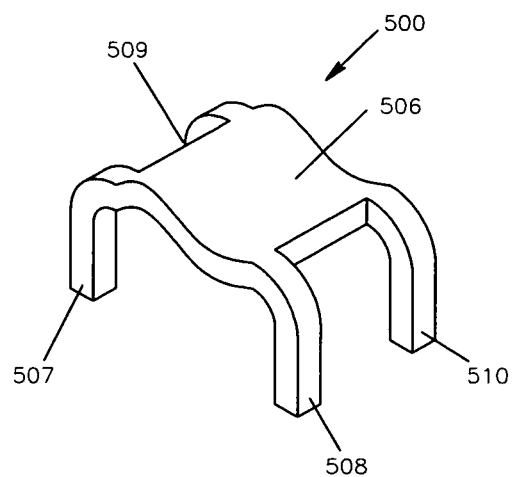
FIG. 18B provides a perspective view of the shape-memory device including the single transition temperature and the permanently formed section after forming the formed section according to the fifth embodiment.
Figure 18C:
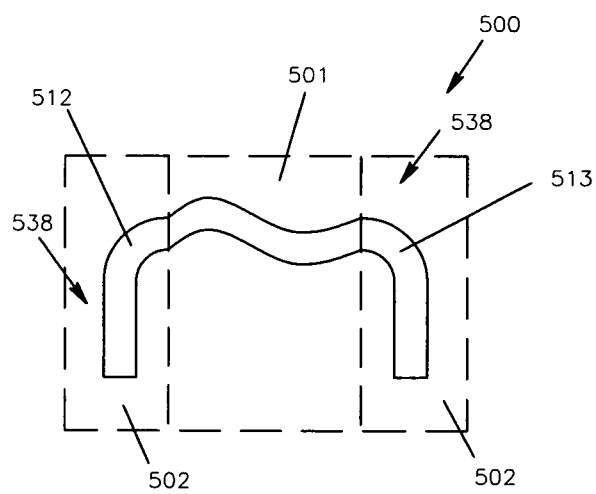
FIG. 18C provides a frontal view of the shape-memory device including the single transition temperature and the permanently formed section after forming the formed section according to the fifth embodiment.

The bridge 506 is disposed within the first portion 501. The bridge 506 is planar in shape, and does not move from a second shape to the first shape. However, the bridge 506 may be formed to adapt to anatomical conditions. As shown in FIGS. 18A-18C, the bridge 506 is formed in a "wave" shape to conform to multiple bones. One of ordinary skill in the art will recognize that virtually any shape form may be utilized to adapt to various anatomical conditions. Illustratively, the bridge 506 may be formed at any angle, any curved shape, channels sections, and the like.

The second portion encompasses the first through fourth legs 507-510 and the first through fourth bends 512-515, as shown in FIGS. 19A-19C. In the second shape 538, the bends 512-515 span substantially ninety degrees, such that the legs 507-515 are substantially perpendicular to the bridge 506. In the first shape 537, the bends 512-515 span approximately sixty degrees. The ends of the first and second legs 507-508 move toward each other as the second portion 502 moves from the second shape 538 to the first shape 537. Substantially simultaneously, the ends of the third and fourth legs 509-510 move toward each other as the second portion 502 moves from the second shape 538 to the first shape 537. Accordingly, contraction forces are created between the legs of the different zones 504-505 of the second portion 502. In this specific example, direct contraction forces are created between the first leg 507 and the second leg 508, and between the third leg 509 and the fourth leg 510.

Figure 20A:
FIG. 20A provides a flowchart illustrating the method steps for manufacturing the shape-memory device with a first portion having an anatomical conformity, and a second portion having a transition temperature according to the fifth embodiment.

FIG. 20A provides the method steps for manufacturing the shape-memory device 500. The process commences with step 62, wherein the shape-memory device 500 is sectioned off to create a first portion 501 and a second portion 502. The portions may be created through the use of any of the methods disclosed in the previous embodiments, including the use of heat treatment jigs having platens with varied thermal conduction capabilities, or platens formed from different materials. In this specific example, no shape setting is required for the first portion 501 because the first portion 501 does not require any transformation. The second portion 502 that includes the shape-memory is then formed into a first shape 537, heat treated, and then deformed to the second shape 538, thereby creating the shape-memory potential. Next, the first portion 501 is permanently deformed to conform to site-specific anatomical conditions, as shown in step 64. One of ordinary skill in the art will recognize that any type of forming process may be utilized to create the permanent deformations.

Figure 20B:
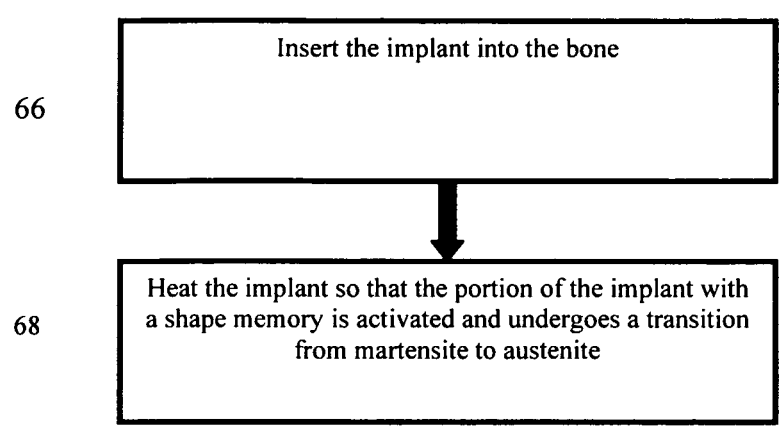
FIG. 20B provides a flowchart illustrating the method steps for utilizing the shape-memory device with the first portion having an anatomical conformity, and the second portion having a transition temperature according to the fifth embodiment.

After the shape-memory device 500 has been manufactured in this fashion, the shape-memory device 500 includes the first portion 501 that is anatomically adapted to the site specific conditions, and a second portion 502 that retains the shape-memory potential. FIG. 20B provides a method flowchart illustrating the method steps for utilizing the shape-memory device 500. As shown in step 66, a surgeon inserts the shape-memory device 500 into a desired location. In this particular example, the desired location would be defined as a location wherein the first portion 501 adapts to the anatomical conditions, and the securing members of the shape-memory device 500 are in the proper securing locations. One of ordinary skill in the art will recognize that the use of staples and the like, as implants, requires the securing of the implant into bones through the use any suitable method, including impaction, or drilling securing holes. Once inserted into the proper location, the second portion 502 is forced to shape change by delivering activation energy to the shape-memory device 500. Upon full activation, the shape-memory device 500 has transitioned to austenite, and the first shape, step 68.

Alternatively, the shape memory device 500 may be formed as a composite shape memory device, wherein the first portion 501 and the second portion 502 are formed as separate components that are subsequently secured to each other. Illustratively, the first portion 501 may be manufactured from a non shape-memory material, deformed to adapt to anatomical conditions, and attached to the second portion 502 that is formed from a shape-memory material, thereby providing all functions of the shape-memory device 500. One of ordinary skill in the art will recognize that the non-shape-memory material utilized in this version of the shape-memory device 500 must be compatible with the human body if the shape-memory device 500 is to be utilized as an implant.

In a further alternative embodiment, a shape memory device 600 includes a multiple strand bridge 612 and legs disposed on the ends of the bridge 612. In this specific example, the multiple strand bridge 612 includes a first lateral member 610, a second lateral member 611, and first through fourth strands 621-624 disposed between the first and second lateral members 610-611. First and second legs 614-615 are disposed on opposite ends of the first lateral member 610, and the third and fourth legs 616-617 are disposed on opposite ends of the second lateral member 611. The legs 614-617 extends to a single side of the bridge 612, such that the legs 614-617 may be secured to adjacent structures, such as a fractured bone, or adjacent bones requiring correction.

Figure 21A:
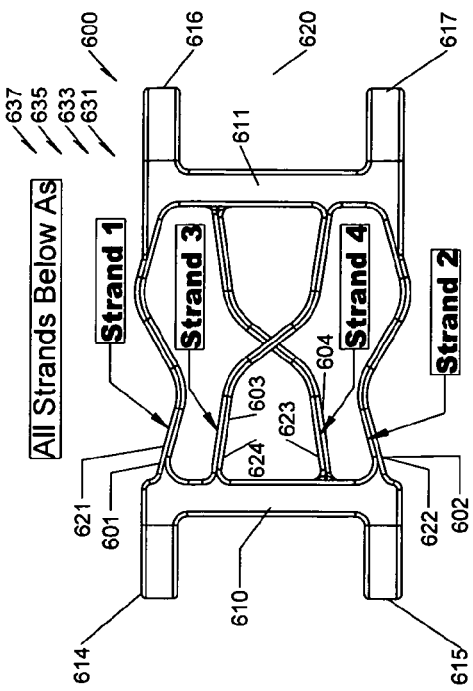
FIG. 21A provides a perspective view of a shape-memory device including a multiple strand bridge and securing members according to a second alternative embodiment.
Figure 21B:
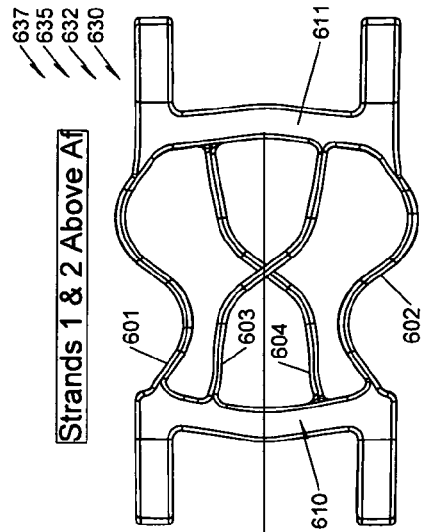
FIG. 21B provides a top view of a shape-memory device including a multiple strand bridge and securing members according to a second alternative embodiment.

As shown in FIGS. 21A-21B, the first through fourth strands 621-624 extend from the first lateral member 610 to the second lateral member 611, and are disposed substantially symmetrical about a mid-plane 620. In this second alternative embodiment, each of the strands 621-624 includes a different transition temperature, such that they activate in a certain order when the activation energy is applied. In this specific example, the first strand 621 has the lowest activation temperature, the second strand 622 has the next highest transition temperature, the third strand 623 has the ext highest transition temperature, and the fourth strand 624 includes the highest transition temperature. Accordingly, a first portion 601 includes the first strand 621, a second portion 602 includes the second strand 622, a third portion 603 includes the third strand 623, and a fourth portion 604 includes the fourth strand 624.

As described in previous embodiments, the shape memory devices formed from shape-memory materials comprise a first shape and a second shape. In this specific example, each of the first through fourth portions 601-604 include a first and second shape, and move from the second shape to an end use shape upon the application of activation energy. As previously disclosed, an end use shape may be any shape moving from a respective second shape up to an including the first shape.

Figure 21C:
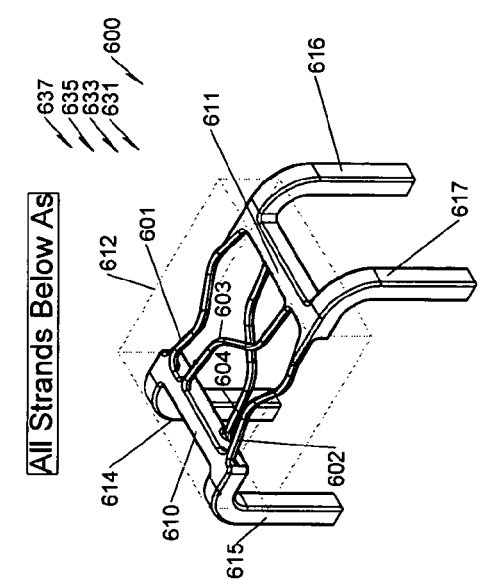
FIG. 21C provides a top view of the shape-memory device having a first portion activated according to the second alternative embodiment.
Figure 21D:
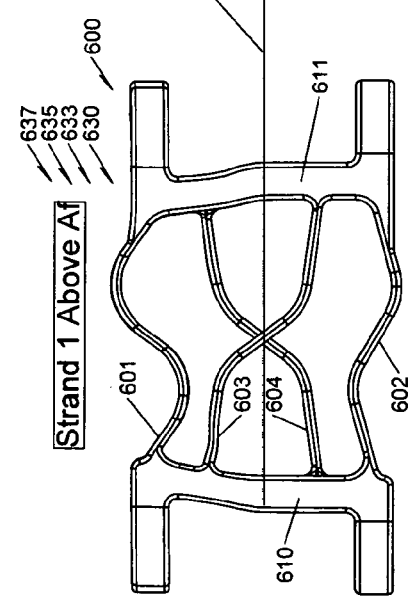
FIG. 21D provides a top view of the shape-memory device having a first and a second portion activated according to the second alternative embodiment.

In operation, the shape memory device 600 functions in similar fashion to the shape memory devices of the previous embodiments, whereby the shape memory device 600 secures to adjacent bones, and then re-orients the adjacent bones. FIG. 21B provides a top view of the shape memory device 600 before activation. At this point, the first through fourth portions 601-604 are at a temperature below $A_s$, and, accordingly, all strands 621-624 are disposed in their respective second shapes 631, 633, 635, and 637. As shown in FIG. 21C, the first strand 621 has reached temperature $A_F$, and the first portion 601 has moved from the second shape 631 to the first shape 630. In this particular example, the first strand 621 contracts when moving from the second shape 631 to the first shape 630. If heat continues to be applied, the second strand 622 reaches temperature $A_F$, as shown in FIG. 21D, and the second strand 622 moves from the second shape 633 to the first shape 632. In this particular example, the second strand 622 contracts when moving from the second shape 633 to the first shape 632. At this point, the first and second strands 621-622 are in their respective first shapes 630 and 632, and the third and fourth strands 623-624 are in their respective second shapes 635 and 637.

The continued application of heat energy to the shape memory device 600 causes the third strand 623 to reach temperature $A_F$, as shown in FIG. 21E, and the third strand 623 moves from the second shape 635 to the first shape 634. In this specific example, the third strand 623 contracts when moving from the second shape 635 to the first shape 634. At this point, the first, second, and third strands 621-623 are in their respective first shapes 630, 632, and 634, and the fourth strand 624 is in the second shape 637.

The continued application of heat energy to the shape memory device 600 causes the fourth strand 624 to reach temperature $A_F$, as shown in FIG. 21F, and the fourth strand 624 moves from the second shape 637 to the first shape 636. In this particular example, the fourth strand 624 contracts when moving from the second shape 637 to the first shape 636. At this point, the first through fourth strands 621-624 are in their respective first shapes 630, 632, 634, and 636.

While this particular example has been shown with first through fourth portions 601-604, one of ordinary skill in the art will recognize that virtually any number of strands may be utilized to accomplish various movements. One of ordinary skill in the art will further recognize that the order of transition may be adjusted by applying heat energy to the strands individually, or by heat treating the shape-memory device 600 in a heat treatment jig as described in the previous embodiments to achieve varied transition temperatures in a single body. Alternatively, the shape memory device 600 may be formed from different materials as described in the previous embodiments.

Although the present invention has been described in terms of the foregoing preferred embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

We claim:

1. A shape-memory device, comprising:
a homogenous shape memory material formed into at least a first portion integral with a second portion, wherein the first portion is treated to transition at a first transition temperature and the second portion is treated to transition at a second transition temperature,
wherein the first portion and the second portion are formed as separate components, whereby the separate components are coupled together to create the shape-memory device having multiple transition temperatures, and
wherein the separate components are formed in layers, wherein each layer has a different transition temperature.

2. The shape-memory device according to claim 1, wherein at least one layer is formed with a multiple transition temperature.

* * * * *